(12) United States Patent
Chen et al.

(10) Patent No.: US 12,378,241 B2
(45) Date of Patent: Aug. 5, 2025

(54) PYRIDINE DERIVATIVE AS FGFR AND VEGFR DUAL INHIBITORS

(71) Applicant: CGeneTech (Suzhou,China) CO., Ltd., Jiangsu (CN)

(72) Inventors: Zhengxia Chen, Shanghai (CN); Meibi Dai, Shanghai (CN); Yang Zhang, Shanghai (CN); Shuhui Chen, Shanghai (CN)

(73) Assignee: CGeneTech (Suzhou,China) CO., Ltd., Jiangsu (CN)

( * ) Notice: Subject to any disclaimer, the term of this patent is extended or adjusted under 35 U.S.C. 154(b) by 727 days.

(21) Appl. No.: 17/629,566

(22) PCT Filed: Jul. 24, 2020

(86) PCT No.: PCT/CN2020/104550
§ 371 (c)(1),
(2) Date: Jan. 24, 2022

(87) PCT Pub. No.: WO2021/018047
PCT Pub. Date: Feb. 4, 2021

(65) Prior Publication Data
US 2022/0267324 A1    Aug. 25, 2022

(30) Foreign Application Priority Data

Jul. 26, 2019   (CN) .......................... 201910684252.3
Dec. 11, 2019   (CN) .......................... 201911266249.6
Mar. 27, 2020   (CN) .......................... 202010230493.3

(51) Int. Cl.
C07D 471/04      (2006.01)
A61P 35/00       (2006.01)

(52) U.S. Cl.
CPC ............ *C07D 471/04* (2013.01); *A61P 35/00* (2018.01)

(58) Field of Classification Search
CPC ............................. C07D 471/04; A61P 35/00
See application file for complete search history.

(56) References Cited

U.S. PATENT DOCUMENTS

| | | | |
|---|---|---|---|
| 8,367,662 B2 * | 2/2013 | Shaw ....................... | A61P 35/00 514/233.2 |
| 8,455,477 B2 | 6/2013 | Katz et al. | |
| 8,481,531 B2 | 7/2013 | Saxty et al. | |
| 8,796,244 B2 | 8/2014 | Berdini et al. | |
| 9,340,514 B2 | 5/2016 | Bifulco, Jr. et al. | |
| 2010/0093718 A1 | 4/2010 | Berdini et al. | |
| 2010/0120761 A1 | 5/2010 | Berdini et al. | |
| 2010/0331296 A1 | 12/2010 | Saxty et al. | |
| 2012/0035152 A1 | 2/2012 | Saxty et al. | |
| 2012/0041000 A1 | 2/2012 | Saxty et al. | |
| 2016/0031855 A1 | 2/2016 | Rajagopalan et al. | |

FOREIGN PATENT DOCUMENTS

| | | |
|---|---|---|
| CN | 101827844 A | 9/2010 |
| JP | 2010513447 A | 4/2010 |
| JP | 2010513448 A | 4/2010 |
| JP | 2011500544 A | 1/2011 |
| JP | 2011500545 A | 1/2011 |
| JP | 2011522866 A | 8/2011 |
| JP | 2011530511 A | 12/2011 |
| JP | 2012524055 A | 10/2012 |
| JP | 2012524056 A | 10/2012 |
| JP | 2015523383 A | 8/2015 |
| JP | 2016515604 A | 5/2016 |
| WO | WO-2008078091 A1 | 7/2008 |
| WO | WO-2009050183 A2 | 4/2009 |
| WO | WO-2018172616 A1 | 9/2018 |
| WO | WO-2020135878 A1 | 7/2020 |

OTHER PUBLICATIONS

Feb. 7, 2023 Japanese First Office Action issued in Japanese Patent Application No. 2022505380.
Dec. 16, 2022 Australian First Office Action issued in Australian Patent Application No. 2020320997.
Oct. 29, 2020 International Search Report issued in International Patent Application No. PCT/CN2020/104550.
Oct. 29, 2020 Written Opinion of the International Searching Authority issued in International Patent Application No. PCT/CN2020/104550.
Goel, R.et al. "Imidazo [1, 2-a] pyridines: Promising Drug Candidate for Antitu-mor Therapy." Current Topics in Medicinal Chemistry., vol. 16, No. 30, Dec. 31, 2016 ? Dec. 31, 2016), ISSN:1568-0266, pp. 3590-3616.
Mar. 18, 2024 First Office Action issued in Korean Patent Application No. 10-2022-7006643.
May 17, 2023 First Office Action issued in Chinese Patent Application No. 202080047757X.
Jun. 1, 2023 First Office Action issued in Canadian Patent Application No. 3145680.
Jun. 26, 2023 Extended European Search Report issued in European Patent Application No. 20847841.2.

(Continued)

*Primary Examiner* — Kamal A Saeed
(74) *Attorney, Agent, or Firm* — Harness, Dickey & Pierce, P.L.C.

(57) ABSTRACT

FGFR and VEGFR dual inhibitors, specifically being a compound represented by formula (I) or a pharmaceutically acceptable salt.

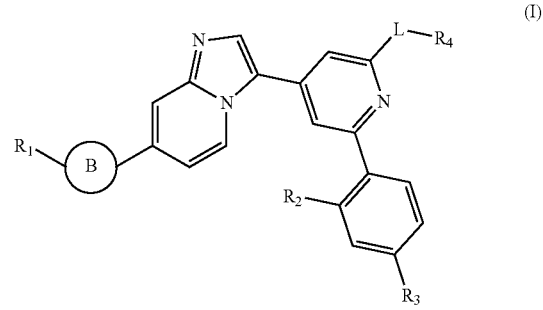

20 Claims, 1 Drawing Sheet

(56) References Cited

OTHER PUBLICATIONS

Hendrik Ungefroren et al., "Signaling Crosstalk of TGF-ß/ALK5 and PAR2/PAR1: A Complex Regulatory Network Controlling Fibrosis and Cancer", Int J Mol Sci. Jun. 2018; 19(6): 1568.
Tim H Holmström et al., "ODM-203, a Selective Inhibitor of FGFR and VEGFR, Shows Strong Antitumor Activity, and Induces Antitumor Immunity", Molecular Cancer Therapeutics, Jan. 2019;18(1):28-38.

* cited by examiner

PYRIDINE DERIVATIVE AS FGFR AND VEGFR DUAL INHIBITORS

CROSS-REFERENCE TO RELATED APPLICATIONS

This application is a U.S. National Phase Application under 35 U.S.C. 371 of International Application No. PCT/CN2020/104550, filed on Jul. 24, 2020, which claims the benefit of Chinese Patent Application No. 201910684252.3, filed on Jul. 26, 2019, Chinese Patent Application No. 201911266249.6, filed on Dec. 11, 2019, and Chinese Patent Application No. 202010230493.3, filed on Mar. 27, 2020. The entire disclosures of the above applications are incorporated herein by reference.

FIELD OF THE INVENTION

The present disclosure relates to FGFR and VEGFR dual inhibitors, specifically being a compound represented by formula (I) or a pharmaceutically acceptable salt.

BACKGROUND

Fibroblast growth factor receptor (FGFR) is a type of receptor protein that specifically binds to fibroblast growth factor (FGF). The FGFRs family includes the following types: FGFR1b, FGFR1c, FGFR2b, FGFR2c, FGFR3b, FGFR3c, FGFR4. Fibroblast growth factor receptor (FGFR) is a class of biologically active substances with the functions of conducting biological signals, regulating cell growth, and participating in tissue repair. It is clinically found that FGFR high expression, mutation or fusion and other abnormalities can cause tumorigenesis and development, such as liver cancer, bladder cancer, lung cancer, breast cancer and other diseases. FGFR binds to the ligand FGF, leading to autophosphorylation of multiple tyrosine residues in the cell, and downstream signals are conducted to, including MEK/MAPK, PLCy/PKC, PI3K/AKT, STATS, etc. Therefore, FGFR is considered to be an important anti-tumor target.

The VEGFR family includes three specific tyrosine kinase receptors: VEGFR-1, VEGFR-2 (KDR) and VEGFR-3. VEGFR-2 is an important regulatory factor of endothelial cell proliferation, vascular permeability increase and angiogenesis promotion caused by VEGF signal conduction, and the affinity of VEGFR-2 and VEGF is greater than VEGFR-1. Studies have shown that only VEGFR-2 is expressed in endothelial cells, and activating VEGFR-2 can effectively stimulate angiogenesis. Therefore, VEGFR-2 is the main target for the development of anti-angiogenesis drugs.

VEGFR and FGFR pathways work together to complete the activation and generation of endothelial cells in angiogenesis. Sometimes VEGF requires the presence of FGF to play its role in promoting angiogenesis. The synergistic effect of FGFR and VEGFR pathways can also inhibit tumor immune evasion and improve the tumor inhibition effect.

Content of the Invention

The present disclosure provides a compound represented by formula (I) or a pharmaceutically acceptable salt thereof,

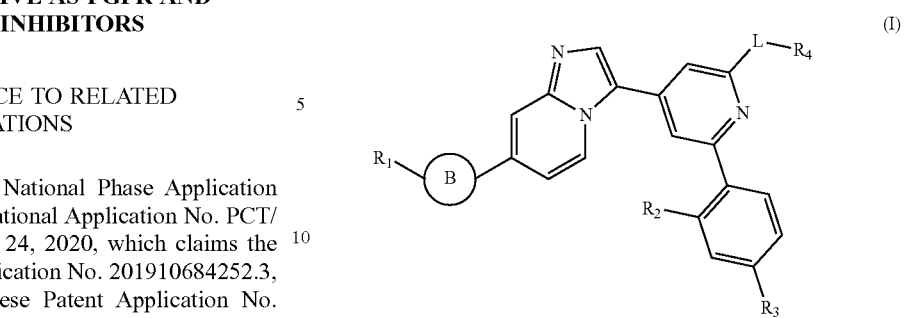

wherein,
$R_1$ is selected from H and $C_{1-3}$ alkyl optionally substituted by 1, 2 or 3 $R_a$;
$R_2$ and $R_3$ are each independently selected from H, F, Cl, Br, I, OH and $NH_2$;
$R_4$ is selected from H, $C_{1-6}$ alkyl and $C_{3-5}$ cycloalkyl, the $C_{1-6}$ alkyl and $C_{3-5}$ cycloalkyl are optionally substituted by 1, 2 or 3 $R_b$;
L is selected from —N($R_5$)C(=O)—, —N($R_5$)S(=O)$_2$—, —N($R_5$)C(=O)N($R_5$)— and —N($R_5$)—;
$R_5$ is each independently selected from H and $C_{1-3}$ alkyl;
ring B is selected from 5-6 membered heteroaryl;
$R_a$ and $R_b$ are each independently selected from H, F, Cl, Br, I, OH, $NH_2$, CN and $CH_3$;
the 5-6 membered heteroaryl contains 1, 2, 3 or 4 heteroatoms or heteroatom groups independently selected from —NH—, —O—, —S— and —N—.

In some embodiments of the present disclosure, the $R_1$ is selected from H, $CH_3$ and $CH_2CH_3$, the $CH_3$ and $CH_2CH_3$ are optionally substituted by 1, 2 or 3 $R_a$, and other variables are as defined in the present disclosure.

In some embodiments of the present disclosure, the $R_1$ is selected from H, $CH_3$, $CH_2OH$, $CH_2CH_2OH$ and $CH_2CH_3$, and other variables are as defined in the present disclosure.

In some embodiments of the present disclosure, the $R_4$ is selected from H, cyclopropyl, $CH_3$, $CH_2CH_3$, $CH(CH_3)_2$, $C(CH_3)_3$ and $CH_2CH_2CH_3$, the cyclopropyl, $CH_3$, $CH_2CH_3$, $CH(CH_3)_2$, $C(CH_3)_3$ and $CH_2CH_2CH_3$ are optionally substituted by 1, 2 or 3 $R_b$, and other variables are as defined in the present disclosure.

In some embodiments of the present disclosure, the $R_4$ is selected from H,

, $CH_3$, $CH_2CH_3$, $CH(CH_3)_2$, $C(CH_3)_3$ and $CH_2CH_2CH_3$, and other variables are as defined in the present disclosure.

In some embodiments of the present disclosure, the $R_5$ is selected from H, $CH_3$ and $CH_2CH_3$, and other variables are as defined in the present disclosure.

In some embodiments of the present disclosure, the L is selected from —NHC(=O)—, —NHC(=O)NH—, —NHS(=O)$_2$— and —NH—, and other variables are as defined in the present disclosure.

In some embodiments of the present disclosure, the -L-$R_4$ is selected from

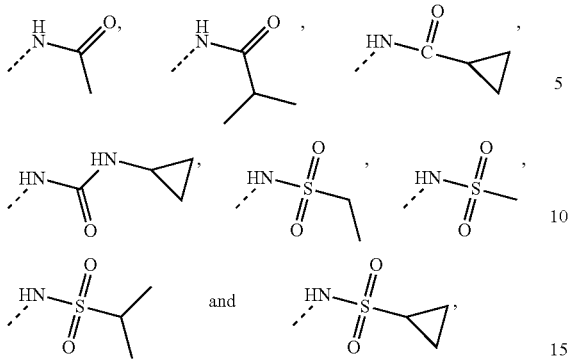

and other variables are as defined in the present disclosure.

In some embodiments of the present disclosure, the ring B is selected from imidazolyl, pyrazolyl, piperidinyl, morpholinyl and tetrahydropyranyl, and other variables are as defined in the present disclosure.

In some embodiments of the present disclosure, the ring B is selected from imidazolyl and pyrazolyl, and other variables are as defined in the present disclosure.

In some embodiments of the present disclosure, the structural moiety

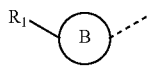

is selected from

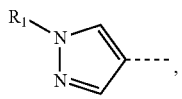

and other variables are as defined in the present disclosure.

In some embodiments of the present disclosure, the structural moiety

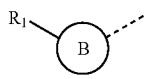

is selected from

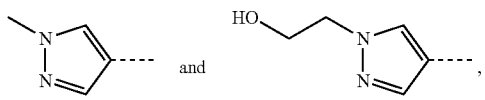

and other variables are as defined in the present disclosure.

The present disclosure provides a compound represented by formula (I) or a pharmaceutically acceptable salt thereof, (I)

wherein,
R$_1$ is selected from H and C$_{1-3}$ alkyl optionally substituted by 1, 2 or 3 R$_a$;
R$_2$ and R$_3$ are each independently selected from H, F, Cl, Br, I, OH, NH$_2$ and CH$_3$;
R$_4$ is selected from H, C$_{1-6}$ alkyl, C$_{1-3}$ alkoxy, C$_{3-5}$ cycloalkyl, tetrahydropyranyl and 1,3-dioxolanyl, wherein, the C$_{1-6}$ alkyl, C$_{1-3}$ alkoxy, C$_{3-5}$ cycloalkyl, tetrahydropyranyl and 1,3-dioxolanyl are optionally substituted by 1, 2 or 3 R$_b$;
L is selected from —N(R$_5$)C(=O)—, —N(R$_5$)S(=O)$_2$—, —N(R$_5$)C(=O)N(R$_5$)—, —N(R$_5$)CH$_2$— and —N(R$_5$)—;
R$_5$ is each independently selected from H and C$_{1-3}$ alkyl;
ring B is selected from pyrazolyl and imidazolyl, the pyrazolyl and imidazolyl are optionally substituted by 1 or 2 R$_6$;
R$_6$ is selected from H and C$_{1-3}$ alkyl;
R$_a$ and R$_b$ are each independently selected from H, F, Cl, Br, I, OH, NH$_2$, CN and CH$_3$.

In some embodiments of the present disclosure, the R$_1$ is selected from H, CH$_3$ and CH$_2$CH$_3$, the CH$_3$ and CH$_2$CH$_3$ are optionally substituted by 1, 2 or 3 R$_a$, and other variables are as defined in the present disclosure.

In some embodiments of the present disclosure, the R$_1$ is selected from H, CH$_3$, CH$_2$OH, CH$_2$CH$_2$OH and CH$_2$CH$_3$, and other variables are as defined in the present disclosure.

In some embodiments of the present disclosure, the R$_4$ is selected from H, cyclopropyl, CH$_3$, CH$_2$CH$_3$, CH(CH$_3$)$_2$, C(CH$_3$)$_3$, CH$_2$CH$_2$CH$_3$, CH$_2$CH(CH$_3$)$_2$, OCH$_3$, OCH$_2$CH$_3$, tetrahydropyranyl and 1,3-dioxolanyl, the cyclopropyl, CH$_3$, CH$_2$CH$_3$, CH(CH$_3$)$_2$, C(CH$_3$)$_3$, CH$_2$CH$_2$CH$_3$, CH$_2$CH(CH$_3$)$_2$, OCH$_3$, OCH$_2$CH$_3$, tetrahydropyranyl and 1,3-dioxolanyl are optionally substituted by 1, 2 or 3 R$_b$, and other variables are as defined in the present disclosure.

In some embodiments of the present disclosure, the R$_4$ is selected from H,

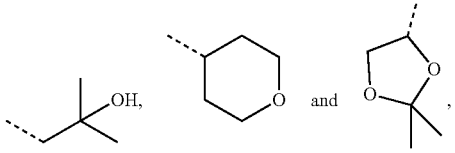

CH$_3$, CH$_2$CH$_3$, CH(CH$_3$)$_2$, C(CH$_3$)$_3$, CH$_2$CH$_2$CH$_3$, OCH$_2$CH$_3$, and other variables are as defined in the present disclosure.

In some embodiments of the present disclosure, the $R_5$ is selected from H, $CH_3$ and $CH_2CH_3$, and other variables are as defined in the present disclosure.

In some embodiments of the present disclosure, the L is selected from —NHC(=O)—, —NHC(=O)NH—, —NHS(=O)$_2$—, —NHCH$_2$— and —NH—, and other variables are as defined in the present disclosure.

In some embodiments of the present disclosure, the -L-$R_4$ is selected from

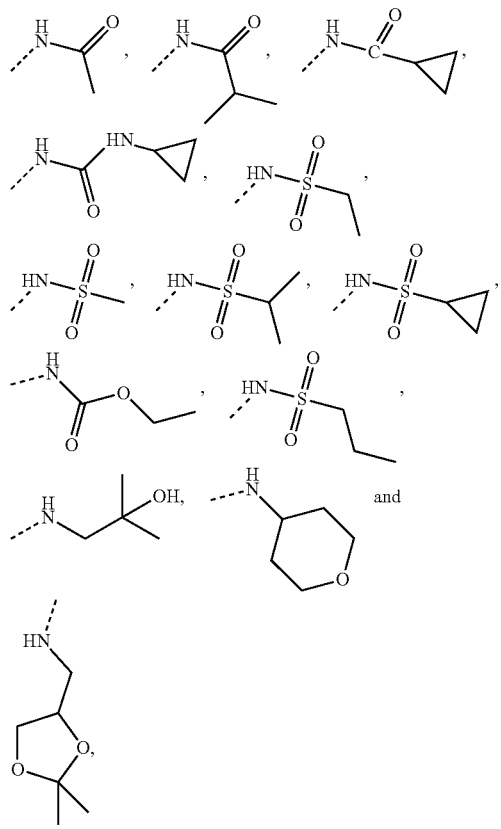

and other variables are as defined in the present disclosure.

In some embodiments of the present disclosure, the ring B is selected from

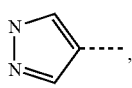

the

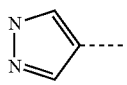

is optionally substituted by 1 or 2 $R_6$, and other variables are as defined in the present disclosure.

In some embodiments of the present disclosure, the ring B is selected from

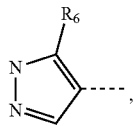

and other variables are as defined in the present disclosure.

In some embodiments of the present disclosure, the structural moiety

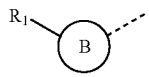

is selected from

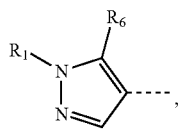

and other variables are as defined in the present disclosure.

In some embodiments of the present disclosure, the structural moiety

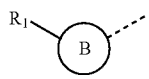

is selected from

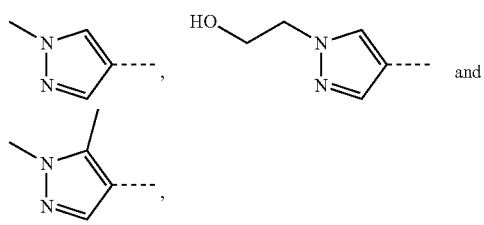

and other variables are as defined in the present disclosure.

The present disclosure provides a compound represented by formula (I) or a pharmaceutically acceptable salt thereof,

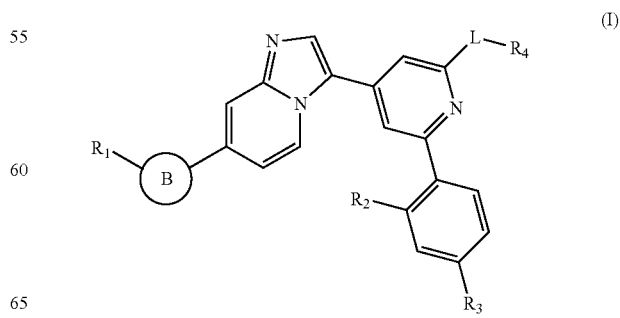

(I)

wherein,
R₁ is selected from H and $C_{1-3}$ alkyl optionally substituted by 1, 2 or 3 $R_a$;
R₂ and R₃ are each independently selected from H, F, Cl, Br, I, OH, $NH_2$ and $CH_3$;
R₄ is selected from H, $C_{1-6}$ alkyl, $C_{1-3}$ alkoxy, $C_{3-5}$ cycloalkyl, tetrahydropyranyl and 1,3-dioxolanyl, the $C_{1-6}$ alkyl, $C_{1-3}$ alkoxy, $C_{3-5}$ cycloalkyl, tetrahydropyranyl and 1,3-dioxolanyl are optionally substituted by 1, 2 or 3 $R_b$;
L is selected from —N(R₅)C(═O)—, —N(R₅)S(═O)₂—, —N(R₅)C(═O)N(R₅)—, —N(R₅)CH₂— and —N(R₅)—;
R₅ is each independently selected from H and $C_{1-3}$ alkyl;
ring B is selected from pyrazolyl and imidazolyl, the pyrazolyl and imidazolyl are optionally substituted by 1 or 2 R₆;
R₆ is selected from H and $C_{1-3}$ alkyl;
$R_a$ and $R_b$ are independently selected from H, F, Cl, Br, I, OH, $NH_2$, CN and $CH_3$.

In some embodiments of the present disclosure, the R₁ is selected from H, $CH_3$ and $CH_2CH_3$, wherein the $CH_3$ and $CH_2CH_3$ are optionally substituted by 1, 2 or 3 $R_a$, and other variables are as defined in the present disclosure.

In some embodiments of the present disclosure, the R₁ is selected from H, $CH_3$, $CH_2OH$, $CH_2CH_2OH$ and $CH_2CH_3$, and other variables are as defined in the present disclosure.

In some embodiments of the present disclosure, the R₄ is selected from H, cyclopropyl, $CH_3$, $CH_2CH_3$, $CH(CH_3)_2$, $C(CH_3)_3$, $CH_2CH_2CH_3$, $CH_2CH(CH_3)_2$, $OCH_3$, $OCH_2CH_3$, tetrahydropyranyl and 1,3-dioxolanyl, the cyclopropyl, $CH_3$, $CH_2CH_3$, $CH(CH_3)_2$, $C(CH_3)_3$, $CH_2CH_2CH_3$, $CH_2CH(CH_3)_2$, $OCH_3$, $OCH_2CH_3$, tetrahydropyranyl and 1,3-dioxolanyl are optionally substituted by 1, 2 or 3 $R_b$, and other variables are as defined in the present disclosure.

In some embodiments of the present disclosure, the R₄ is selected from H,

$CH_3$, $CH_2CH_3$, $CH(CH_3)_2$, $C(CH_3)_3$, $CH_2CH_2CH_3$, $OCH_2CH_3$,

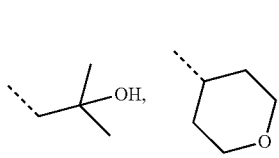

and other variables are as defined in the present disclosure.

In some embodiments of the present disclosure, the R₅ is selected from H, $CH_3$ and $CH_2CH_3$, and other variables are as defined in the present disclosure.

In some embodiments of the present disclosure, the L is selected from —NHC(═O)—, —NHC(═O)NH—, —NHS(═O)₂—, —NHCH₂— and —NH—, and other variables are as defined in the present disclosure.

In some embodiments of the present disclosure, the -L-R₄ is selected from

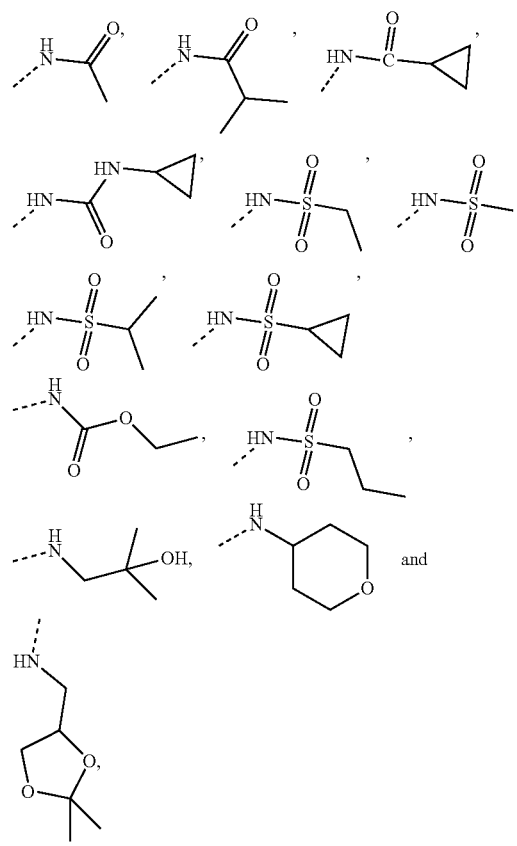

and other variables are as defined in the present disclosure.

In some embodiments of the present disclosure, the ring B is selected from

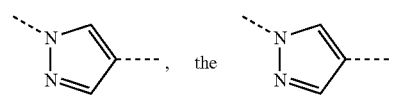

is optionally substituted by 1 or 2 R₆, and other variables are as defined in the present disclosure.

In some embodiments of the present disclosure, the ring B is selected from

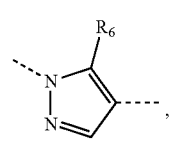

and other variables are as defined in the present disclosure.

In some embodiments of the present disclosure, the structural moiety

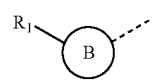

is selected from

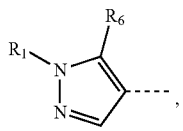

and other variables are as defined in the present disclosure.

In some embodiments of the present disclosure, the structural moiety

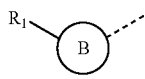

is selected from

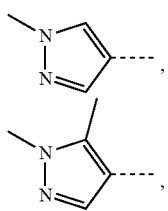

and other variables are as defined in the present disclosure.

There are also some embodiments of the present disclosure that come from any combination of the above-mentioned variables.

In some embodiments of the present disclosure, the compound or the pharmaceutically acceptable salt thereof, is selected from

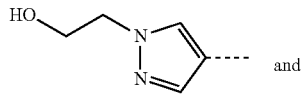

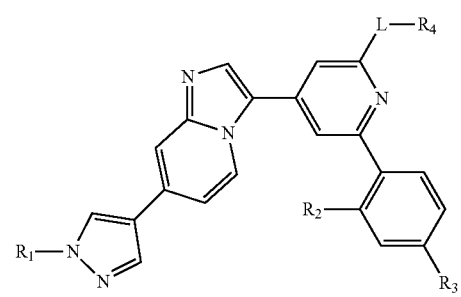

(I-1)

(III-1)

wherein,
R₁, R₂, R₃, L and R₄ are as defined in the present disclosure.

In some embodiments of the present disclosure, the compound or the pharmaceutically acceptable salt thereof, is selected from

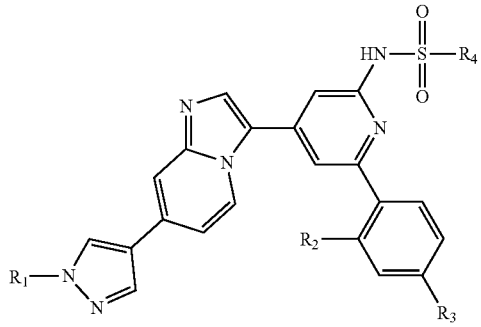

(I-1a)

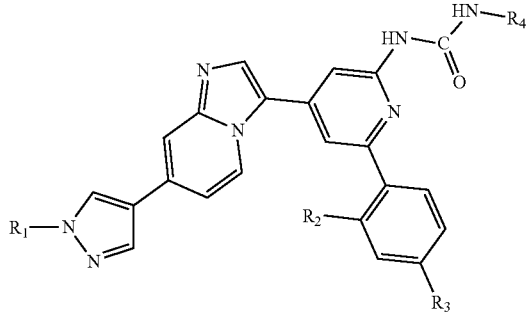

(I-1b)

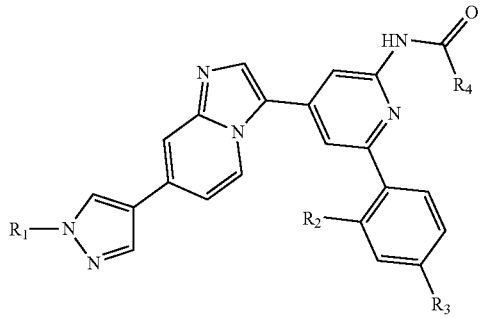

(I-1c)

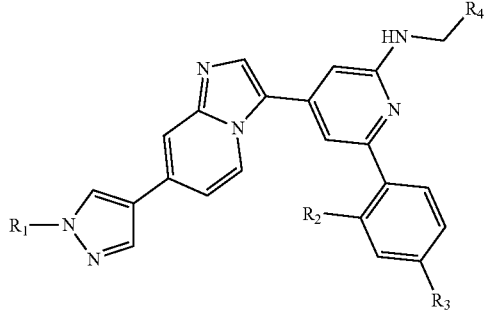

(II-1a)

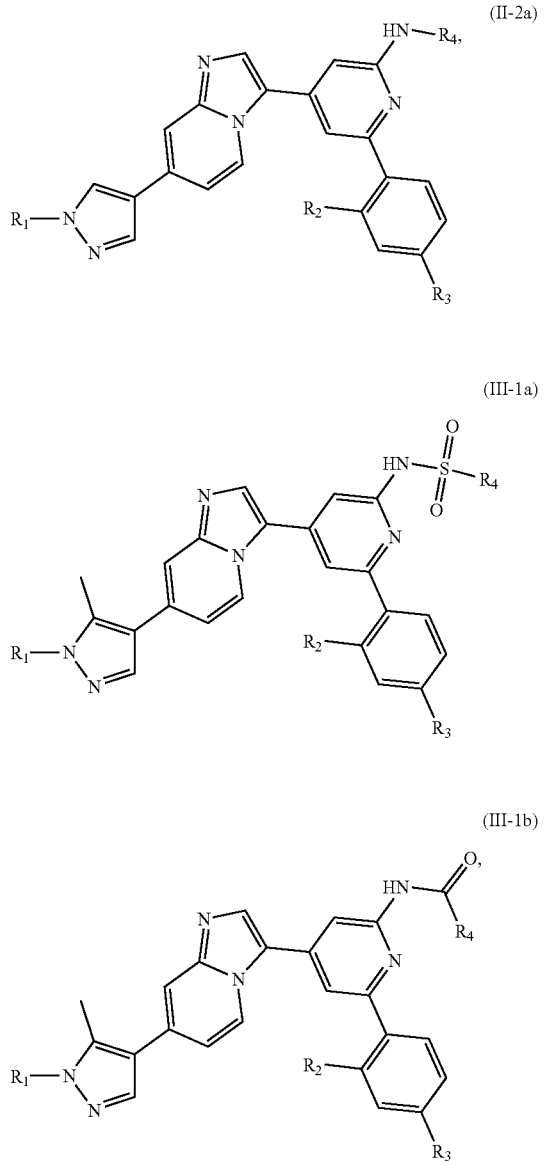
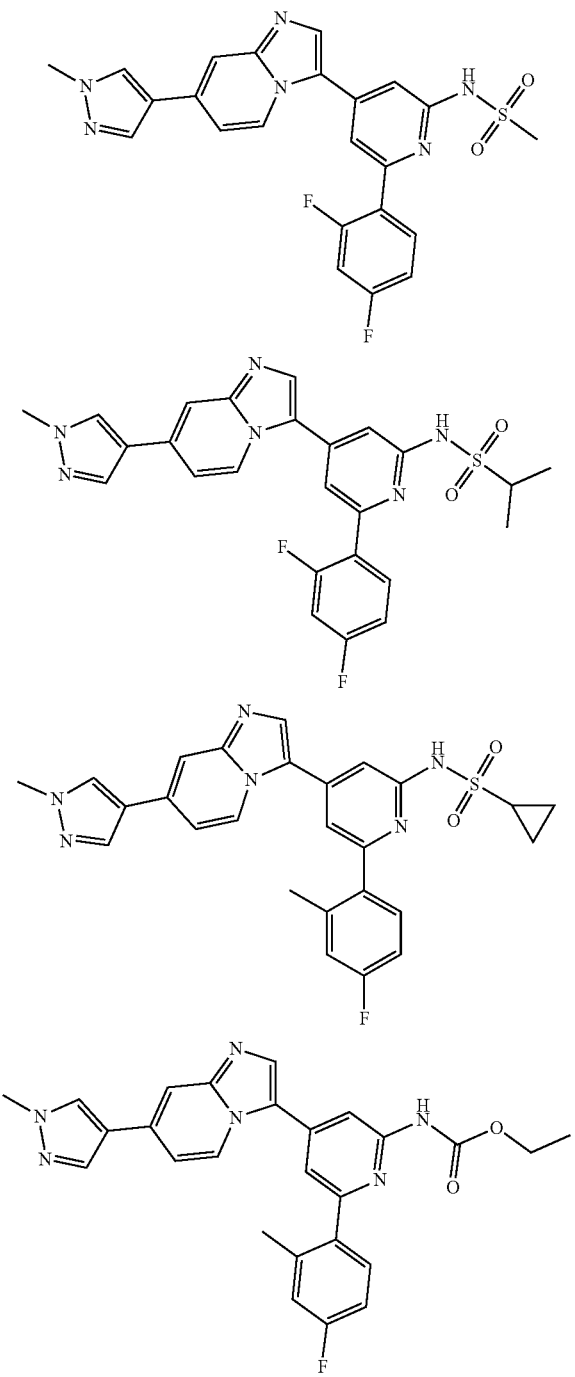
wherein,
R₁, R₂, R₃ and R₄ are as defined in the present disclosure.
The present disclosure provides a compound represented by the following formula or a pharmaceutically acceptable salt thereof,
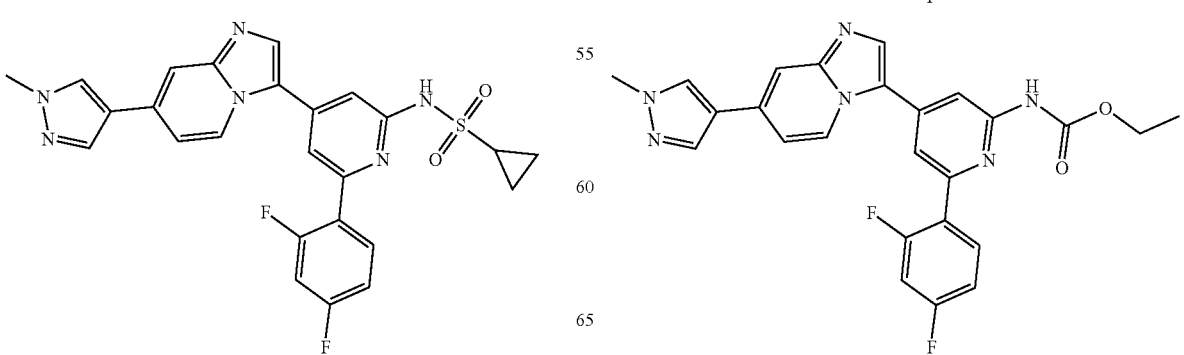

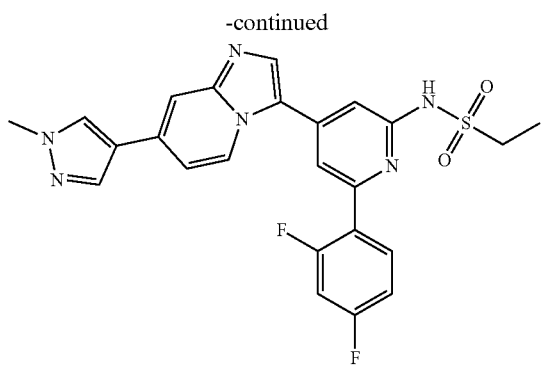

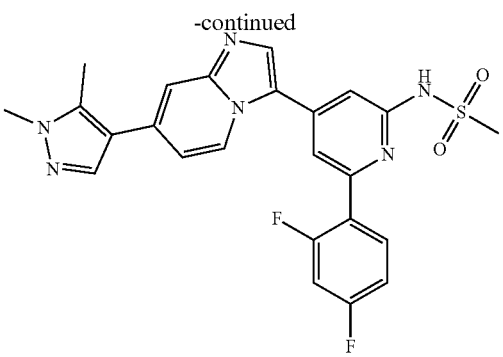

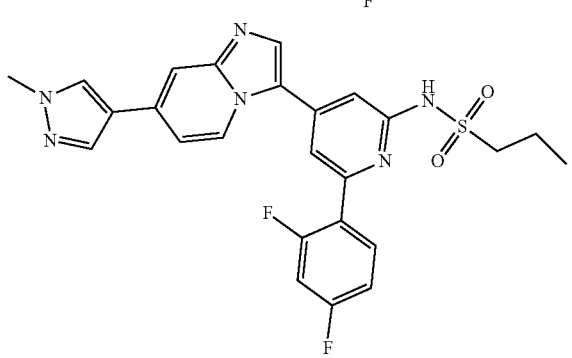

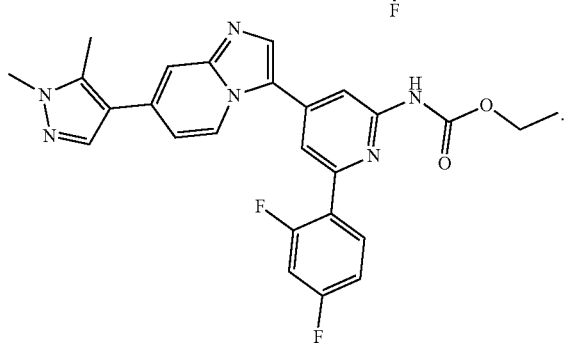

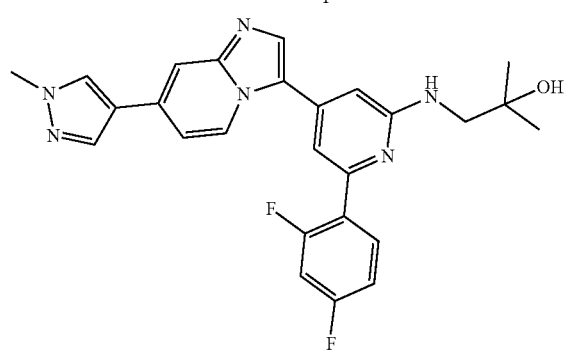

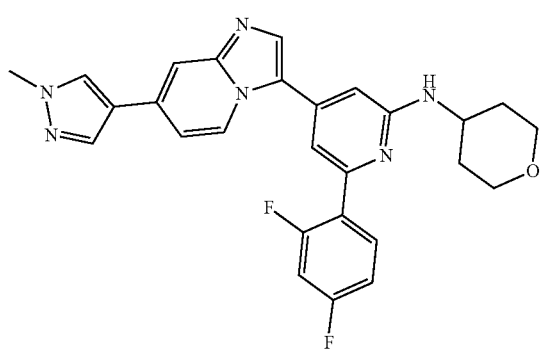

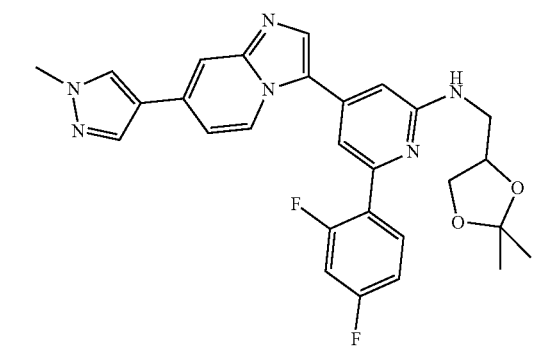

The present disclosure also provides a pharmaceutical composition comprising a therapeutically effective amount of the above-mentioned compound or the pharmaceutically acceptable salt thereof as an active ingredient and a pharmaceutically acceptable carrier.

The present disclosure also provides a use of the above-mentioned compound or the pharmaceutically acceptable salt thereof or the above-mentioned pharmaceutical composition in the preparation of a medicament related to FGFR and VEGFR dual inhibitor.

In some embodiments of the present disclosure, in the above-mentioned use, the medicament related to FGFR and VEGFR dual inhibitor are medicaments for solid tumors.

Definition and Description

Unless otherwise specified, the following terms and phrases when used herein have the following meanings. A specific term or phrase should not be considered indefinite or unclear in the absence of a particular definition, but should be understood in the ordinary sense. When a trade name appears herein, it is intended to refer to its corresponding commodity or active ingredient thereof. The term "pharmaceutically acceptable" is used herein in terms of those compounds, materials, compositions, and/or dosage forms, which are suitable for use in contact with human and animal tissues within the scope of reliable medical judgment, with no excessive toxicity, irritation, an allergic reaction or other problems or complications, commensurate with a reasonable benefit/risk ratio.

The term "pharmaceutically acceptable salt" refers to a salt of the compound of the present disclosure that is prepared by reacting the compound having a specific substituent of the present disclosure with a relatively non-toxic acid or base. When the compound of the present disclosure contains a relatively acidic functional group, a base addition salt can be obtained by bringing the neutral form of the compound into contact with a sufficient amount of base in a pure solution or a suitable inert solvent. The pharmaceutically acceptable base addition salt includes a salt of sodium, potassium, calcium, ammonium, organic ammonia or magnesium, or similar salts. When the compound of the present disclosure contains a relatively basic functional group, an acid addition salt can be obtained by bringing the neutral form of the compound into contact with a sufficient amount of acid in a pure solution or a suitable inert solvent. Examples of the pharmaceutically acceptable acid addition salt include an inorganic acid salt, wherein the inorganic acid includes, for example, hydrochloric acid, hydrobromic acid, nitric acid, carbonic acid, bicarbonate, phosphoric acid, monohydrogen phosphate, dihydrogen phosphate, sulfuric acid, hydrogen sulfate, hydroiodic acid, phosphorous acid, and the like; and an organic acid salt, wherein the organic acid includes, for example, acetic acid, propionic acid, isobutyric acid, maleic acid, malonic acid, benzoic acid, succinic acid, suberic acid, fumaric acid, lactic acid, mandelic acid, phthalic acid, benzenesulfonic acid, p-toluenesulfonic acid, citric acid, tartaric acid, and methanesulfonic acid, and the like; and salts of amino acid (such as arginine and the like), and a salt of an organic acid such as glucuronic acid and the like. Certain specific compounds of the present disclosure contain both basic and acidic functional groups, thus can be converted to any base or acid addition salt.

The pharmaceutically acceptable salt of the present disclosure can be prepared from the parent compound that contains an acidic or basic moiety by conventional chemical method. Generally, such salt can be prepared by reacting the free acid or base form of the compound with a stoichiometric amount of an appropriate base or acid in water or an organic solvent or a mixture thereof.

In addition to salt form, the compound provided by the present disclosure also has a prodrug form. The prodrugs of the compounds described herein can easily undergo chemical changes under physiological conditions to transform into the compounds of the disclosure. In addition, prodrugs can be converted to the compounds of the present disclosure by chemical or biochemical methods in the in vivo environment.

Certain compounds of the present disclosure may exist in unsolvated or solvated forms, including hydrated forms. Generally, the solvated form is equivalent to the unsolvated form, and both are in the scope of the present disclosure.

Optically active (R)- and (S)-isomer, or D and L isomer can be prepared using chiral synthesis or chiral reagents or other conventional techniques. If one kind of enantiomer of a certain compound of the present disclosure is to be obtained, the pure desired enantiomer can be obtained by asymmetric synthesis or derivative action of chiral auxiliary followed by separating the resulting diastereomeric mixture and cleaving the auxiliary group. Alternatively, when the molecule contains a basic functional group (such as amino) or an acidic functional group (such as carboxyl), the compound reacts with an appropriate optically active acid or base to form a salt of the diastereomeric isomer which is then subjected to diastereomeric resolution through the conventional method in the art to give the pure enantiomer. In addition, the enantiomer and the diastereoisomer are generally isolated through chromatography which uses a chiral stationary phase and optionally combines with a chemical derivative method (such as carbamate generated from amine). The compound of the present disclosure may contain an unnatural proportion of atomic isotope at one or more than one atom(s) that constitute the compound. For example, the compound can be radiolabeled with a radioactive isotope, such as tritium ($^3$H), iodine-125 ($^{125}$I) or C-14 ($^{14}$C). For another example, deuterated drugs can be formed by replacing hydrogen with heavy hydrogen, the bond formed by deuterium and carbon is stronger than that of ordinary hydrogen and carbon, compared with non-deuterated drugs, deuterated drugs have the advantages of reduced toxic and side effects, increased drug stability, enhanced efficacy, extended biological half-life of drugs, etc. All isotopic variations of the compound of the present disclosure, whether radioactive or not, are encompassed within the scope of the present disclosure.

The term "optional" or "optionally" means that the subsequent event or condition may occur but not requisite, that the term includes the instance in which the event or condition occurs and the instance in which the event or condition does not occur.

The term "substituted" means one or more than one hydrogen atom(s) on a specific atom are substituted with the substituent, including deuterium and hydrogen variables, as long as the valence of the specific atom is normal and the substituted compound is stable. When the substituent is oxygen (i.e., =O), it means two hydrogen atoms are substituted. Positions on an aromatic ring cannot be substituted with a ketone. The term "optionally substituted" means an atom can be substituted with a substituent or not, unless otherwise specified, the type and number of the substituent may be arbitrary as long as being chemically achievable.

When any variable (such as R) occurs in the constitution or structure of the compound more than once, the definition of the variable at each occurrence is independent. Thus, for example, if a group is substituted with 0-2 R, the group can be optionally substituted with up to two R, wherein the definition of R at each occurrence is independent. Moreover, a combination of the substituent and/or the variant thereof is allowed only when the combination results in a stable compound.

When the number of a linking group is 0, such as —(CRR)$_0$—, it means that the linking group is a single bond.

When one of the variables is selected from a single bond, it means that the two groups linked by the single bond are connected directly. For example, when L in A-L-Z represents a single bond, the structure of A-L-Z is actually A-Z.

When a substituent is vacant, it means that the substituent does not exist, for example, when X is vacant in A-X, the structure of A-X is actually A. When the enumerative substituent does not indicate by which atom it is linked to the group to be substituted, such substituent can be bonded by any atom thereof. For example, when pyridyl acts as a substituent, it can be linked to the group to be substituted by any carbon atom on the pyridine ring. When the enumerative linking group does not indicate the direction for linking, the direction for linking is arbitrary, for example, the linking group L contained in

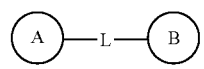

is -M-W-, then -M-W- can link ring A and ring B to form

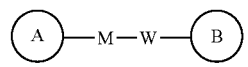

in the direction same as left-to-right reading order, and form

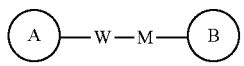

in the direction contrary to left-to-right reading order. A combination of the linking groups, substituents and/or variables thereof is allowed only when such combination can result in a stable compound.

Unless otherwise specified, the term "$C_{1-6}$ alkyl" refers to a linear or branched saturated hydrocarbon group containing 1 to 6 carbon atoms. The $C_{1-6}$ alkyl includes $C_{1-5}$, $C_{1-4}$, $C_{1-3}$, $C_{1-2}$, $C_{2-6}$, $C_{2-4}$, $C_6$ and $C_5$ alkyl groups and the like. It can be monovalent (such as methyl), divalent (such as methylene) or multivalent (such as methine). Examples of $C_{1-6}$ alkyl include but are not limited to methyl (Me), ethyl (Et), propyl (including n-propyl and isopropyl), butyl (including n-butyl, isobutyl, s-butyl, and t-butyl), pentyl (including n-pentyl, isopentyl and neopentyl), hexyl, etc.

Unless otherwise specified, the term "$C_{1-3}$ alkyl" refers to a linear or branched saturated hydrocarbon group containing 1 to 3 carbon atoms. The $C_{1-3}$ alkyl group includes $C_{1-2}$ and $C_{2-3}$ alkyl groups and the like; it can be monovalent (such as methyl), divalent (such as methylene) or multivalent (such as methine). Examples of $C_{1-3}$ alkyl include, but are not limited to methyl (Me), ethyl (Et), propyl (including n-propyl and isopropyl), etc.

Unless otherwise specified, the term "$C_{1-3}$ alkoxy" refers to an alkyl group containing 1 to 3 carbon atoms that are connected to the rest of the molecule through an oxygen atom. The $C_{1-3}$ alkoxy includes $C_{1-2}$, $C_{2-3}$, $C_3$ and $C_2$ alkoxy, etc. Examples of $C_{1-3}$ alkoxy include, but are not limited to, methoxy, ethoxy, propoxy (including n-propoxy and iso-propoxy), etc.

Unless otherwise specified, "$C_{3-5}$ cycloalkyl" refers to a saturated cyclic hydrocarbon group composed of 3 to 5 carbon atoms, which is a monocyclic ring system, and the $C_{3-5}$ cycloalkyl includes $C_{3-4}$ and $C_{4-5}$ cycloalkyl, etc.; it can be monovalent, divalent or multivalent. Examples of $C_{3-5}$ alkoxy include, but are not limited to, cyclopropyl, cyclobutyl, cyclopentyl, etc.

Unless otherwise specified, the terms "5-6 membered heteroaryl ring" and "5-6 membered heteroaryl" can be used interchangeably in the present disclosure. The term "5-6 membered heteroaryl" refers to a monocyclic group consisting of 5 to 6 ring atoms, which has a conjugated 7π-electron system, wherein, 1, 2, 3 or 4 ring atoms are heteroatoms independently selected from O, S and N, and the rest are carbon atoms. Wherein, the nitrogen atom is optionally quaternized, the nitrogen and sulfur heteroatoms can optionally be oxidized (i.e. NO and $S(O)_p$, p is 1 or 2). The 5-6 membered heteroaryl can be attached to the rest of the molecule through a heteroatom or a carbon atom. The 5-6 membered heteroaryl includes 5-membered and 6-membered heteroaryls. Examples of the 5-6 membered heteroaryl include but are not limited to pyrrolyl (including N-pyrrolyl, 2-pyrrolyl, 3-pyrrolyl, etc.), pyrazolyl (including 2-pyrazolyl and 3-pyrrolyl, etc.) imidazolyl (including N-imidazolyl, 2-imidazolyl, 4-imidazolyl and 5-imidazolyl, etc.), oxazolyl (including 2-oxazolyl, 4-oxazolyl and 5-Oxazolyl, etc.), triazolyl (1H-1,2,3-triazolyl, 2H-1,2,3-triazolyl, 1H-1,2,4-triazolyl and 4H-1,2,4-triazolyl, etc.), tetrazolyl, isoxazolyl (3-isoxazolyl, 4-isoxazolyl and 5-isoxazolyl, etc.), thiazolyl (including 2-thiazolyl, 4-thiazolyl and 5-thiazolyl, etc.), furyl (including 2-furyl and 3-furyl, etc.), thienyl (including 2-thienyl and 3-thienyl, etc.), pyridyl (including 2-pyridyl, 3-pyridyl and 4-pyridyl, etc.), pyrazinyl or pyrimidinyl (including 2-pyrimidinyl and 4-pyrimidinyl, etc.).

The term "leaving group" refers to a functional group or atom which can be replaced by another functional group or atom through a substitution reaction (such as affinity substitution reaction). For example, representative leaving groups include triflate; chlorine, bromine, and iodine; sulfonate group, such as mesylate, tosylate, p-bromobenzenesulfonate, p-toluenesulfonates and the like; acyloxy, such as acetoxy, trifluoroacetoxy and the like.

The term "protecting group" includes, but is not limited to "amino protecting group", "hydroxy protecting group" or "thio protecting group". The term "amino protecting group" refers to a protecting group suitable for blocking the side reaction on the nitrogen of an amino. Representative amino protecting groups include, but are not limited to: formyl; acyl, such as alkanoyl (e.g., acetyl, trichloroacetyl or trifluoroacetyl); alkoxycarbonyl, such as tert-butoxycarbonyl (Boc); arylmethoxycarbonyl such as benzyloxycarbonyl (Cbz) and 9-fluorenylmethoxycarbonyl (Fmoc); arylmethyl, such as benzyl (Bn), trityl (Tr), 1,1-bis-(4'-methoxyphenyl) methyl; silyl, such as trimethylsilyl (TMS) and tert-butyldimethylsilyl (TBS) and the like. The term "hydroxy protecting group" refers to a protecting group suitable for blocking the side reaction on hydroxy. Representative hydroxy protecting groups include, but are not limited to: alkyl, such as methyl, ethyl, and tert-butyl; acyl, such as alkanoyl (e.g., acetyl); arylmethyl, such as benzyl (Bn), p-methoxybenzyl (PMB), 9-fluorenylmethyl (Fm), and diphenylmethyl (benzhydryl, DPM); silyl, such as trimethylsilyl (TMS) and tert-butyl dimethyl silyl (TBS) and the like.

The compounds of the present disclosure can be prepared by a variety of synthetic methods known to those skilled in the art, including the specific embodiments listed below, the embodiments formed by their combination with other chemical synthesis methods, and equivalent alternatives known to those skilled in the art, preferred implementations include but are not limited to the embodiments of the present disclosure.

The solvents used in the present disclosure are commercially available. The present disclosure uses the following abbreviations: aq stands for aqueous solution; eq stands for equivalent, equivalent; DCM stands for dichloromethane; PE stands for PE; DMF stands for N,N-dimethylformamide; DMSO stands for dimethyl sulfoxide; EtOAc stands for ethyl acetate; EtOH stands for ethanol; MeOH stands for methanol; CBz stands for benzyloxycarbonyl which is an amine protecting group; BOC stands for tert-butoxycarbonyl which is an amine protecting group; HOAc stands for acetic acid; r.t. stands for room temperature; O/N stands for overnight; THF stands for tetrahydrofuran; $Boc_2O$ stands for di-tert-butyl dicarbonate; TFA stands for trifluoroacetic acid; iPrOH stands for 2-propanol; mp stands for melting point; Xantphos stands for 4,5-bisdiphenylphosphine-9,9-dimethylxanthene; $Pd(dppf)Cl_2$ represents [1,1'-bis(diphenylphosphino)ferrocene] palladium dichloride; DIEA represents N,N'-diisopropyl ethyl amine; NIS stands for N-iodosuccinimide.

The compounds of the present disclosure are named according to the conventional naming principles in the art or by ChemDraw® software, and the commercially available compounds use the supplier catalog names.

Technical Effect

The compound of the present disclosure has excellent FGFRs, VEGFR2 kinase activity; It is unexpectedly found that the introduction of heterocyclic nitrogen atoms in the middle aromatic ring of the compound of the present disclosure can significantly improve the metabolic stability of the compound in vivo, and greatly increase the drug exposure of oral absorption, which is highly possible to show a better therapeutic effect in clinical practice; the compound of the present disclosure shows an excellent tumor therapeutic effect.

DETAILED DESCRIPTION OF THE EMBODIMENT

Figure 1:
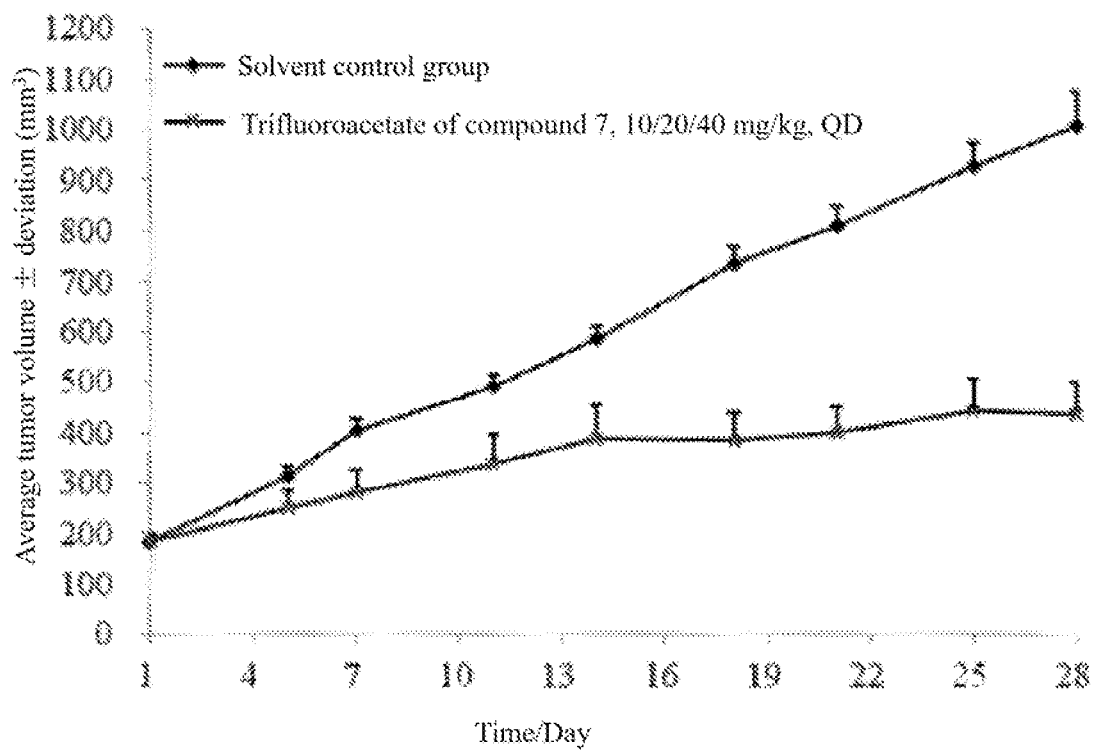
FIG. 1: The tumor volume growth curve of each group during the administration period.

The present disclosure will be specifically described below by way of embodiments, but the scope of the present disclosure is not limited thereto. The present disclosure has been described in detail herein, wherein specific embodiments thereof are also disclosed, for those skilled in the art, it is obvious that various changes and improvements can be made to the specific embodiments of the present disclosure without departing from the spirit and scope of the present disclosure.

Comparative Example 1

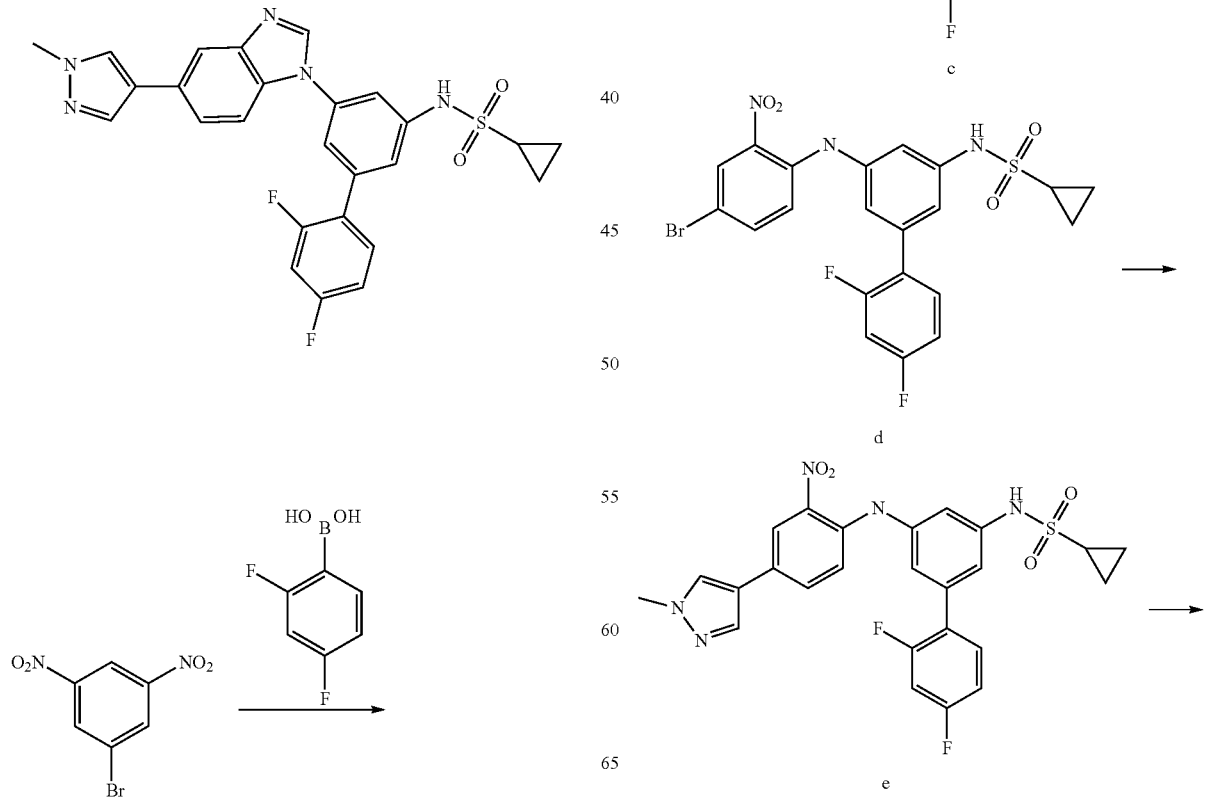

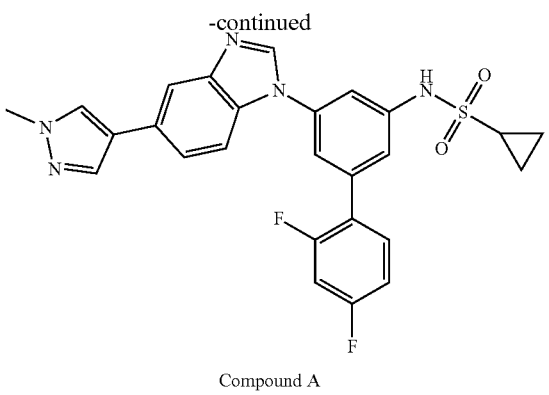

Compound A

Step 1

3,5-dinitrobromobenzene (10 g, 40.49 mmol) and (2,4-difluoro)phenylboronic acid (6.39 g, 40.49 mmol) were dissolved in a mixed solution of water (2 mL) and acetonitrile (120 mL), and palladium acetate (454.46 mg, 2.02 mmol) and triethylamine (12.29 g, 121.46 mmol, 16.91 mL) were added, the reaction mixture was stirred at 85° C. for 16 hours, then directly evaporated to dryness to obtain a crude solid product, the crude solid product was purified by column chromatography (PE:EA=5:1) to obtain compound a.

$^1$H NMR (400 MHz, CDCl$_3$) δ 9.06 (t, J=2.00 Hz, 1H), 8.72 (dd, J=1.92, 1.10 Hz, 2H), 7.54 (td, J=8.74, 6.32 Hz, 1H), 7.00-7.15 (m, 2H).

Step 2

Compound a (6.5 g, 23.20 mmol) was dissolved in a hydrogenation flask containing EtOAc (65 mL) and Pd/C (1 g, 23.20 mmol, 10% purity) was added thereto. The reaction mixture in the flask charged with hydrogen (50 Psi) (46.77 mg, 23.20 mmol, 1 eq) was stirred at 45° C. for 16 hours. The reaction mixture was filtered, and the filtrate was evaporated to dryness to obtain compound b.

LCMS (ESI) m/z: 220.9 [M+1]$^+$;

$^1$H NMR (400 MHz, DMSO-d$_6$) δ 7.36-7.45 (m, 1H), 7.20-7.30 (m, 1H), 7.10 (td, J=8.52, 2.44 Hz, 1H), 5.92 (d, J=1.52 Hz, 2H), 5.86 (d, J=1.82 Hz, 1H), 4.84 (s, 4H).

Step 3

DIEA (417.28 mg, 3.23 mmol, 562.37 μL), ethoxytrimethylsilane (2.29 g, 19.37 mmol) were added to a solution of compound b (2.37 g, 10.76 mmol) in DMSO (15 mL), and 4-bromo-1-fluoro-2-nitro-benzene (2.37 g, 10.76 mmol, 1.32 mL) was added thereto, the reaction mixture was stirred at 100° C. for 16 hours. The reaction mixture was added to 100 mL of water and stirred, and a large number of solids were precipitated. The resulting mixture was filtered off with suction under reduced pressure to collect the filter cake, 20 mL of anhydrous toluene was added to the filter cake, and the filter cake was evaporated to dryness to obtain compound c.

LCMS (ESI) m/z: 419.9 [M+1]$^+$;

$^1$H NMR (400 MHz, CDCl$_3$) δ 9.40 (s, 1H), 8.33 (d, J=2.26 Hz, 1H), 7.33-7.46 (m, 2H), 7.21-7.25 (m, 2H), 7.11-7.19 (m, 1H), 6.86-6.97 (m, 2H), 6.76 (d, J=1.52 Hz, 1H), 6.68 (d, J=1.76 Hz, 1H), 6.56 (t, J=2.02 Hz, 1H).

Step 4

Cyclopropylsulfonyl chloride (1.66 g, 11.78 mmol) was added to a suspension of compound c (4.5 g, 10.71 mmol) in pyridine (30 mL) under nitrogen protection, and the reaction mixture was stirred at 20° C. for 2 hours. Acetic acid (34.6 mL) was added to the reaction mixture, then water (250 mL) was added thereto, and the mixture was extracted with ethyl acetate (150 mL*2). The organic phases were combined, dried over anhydrous sodium sulfate, and concentrated under reduced pressure to obtain compound d.

LCMS (ESI) m/z: 525.8 [M+1]$^+$

Step 5

Triphenylphosphine (1.40 g, 5.34 mmol), palladium acetate (359.67 mg, 1.60 mmol), and potassium carbonate (3.84 g, 27.77 mmol) were added to a solution of compound d (5.6 g, 10.68 mmol) and 1-methyl-4-pyrazole borate (2.78 g, 13.35 mmol) in dimethyl sulfoxide (110 mL)/water (30 mL), the reaction mixture was stirred at 100° C. for 16 hours under nitrogen protection. Under stirring, water (200 mL) was added to the reaction mixture, and a solid was precipitated, the resulting mixture was filtered off with suction under reduced pressure to collect the filter cake, which was transferred to a single-necked flask with dichloromethane, and then concentrated under reduced pressure to obtain a crude product. The crude product was purified by column (flash silica gel column chromatography) with PE/ethyl acetate=0/1 to obtain compound e.

LCMS (ESI) m/z: 526.4 [M+3]$^+$;

$^1$H NMR (400 MHz, CDCl$_3$) δ 9.45 (s, 1H), 8.29 (d, J=2.02 Hz, 1H), 7.73 (s, 1H), 7.62 (s, 1H), 7.53-7.58 (m, 1H), 7.37-7.48 (m, 2H), 7.16-7.24 (m, 3H), 6.90-7.01 (m, 2H), 6.71 (s, 1H), 3.96 (s, 3H), 2.52-2.65 (m, 1H), 1.22-1.26 (m, 2H), 0.98-1.11 (m, 2H).

Step 6

Pd/C (1 g, 5.33 mmol, 10% purity) was added to a solution of compound e (2.8 g, 5.33 mmol, 1 eq) in formic acid (30 mL), and the reaction mixture was stirred at 30° C. for 16 hours under a hydrogen balloon (15 psi) atmosphere. The reaction mixture was filtered through celite after the reaction was complete, and the filtrate was concentrated under reduced pressure to obtain a crude product. The crude product was subjected to high performance liquid chromatography (chromatographic column: YMC-Triart Prep C18 150*40 mm*7 μm; mobile phase: [water (0.1% trifluoroacetic acid)-acetonitrile]; B (acetonitrile) %: 35%-50%, 10 min) to obtain the trifluoroacetate salt of compound A. The trifluoroacetate salt of compound A was added to a sodium bicarbonate solution, and extracted with ethyl acetate. The organic phase was dried over anhydrous sodium sulfate and concentrated under reduced pressure to obtain compound A.

LCMS (ESI) m/z: 506.0 [M+1]$^+$;

$^1$H NMR (400 MHz, DMSO-d$_6$) δ 10.25 (br s, 1H), 8.65 (s, 1H), 8.19 (s, 1H), 7.99 (s, 1H), 7.94 (s, 1H), 7.71-7.81 (m, 1H), 7.64-7.70 (m, 1H), 7.55-7.63 (m, 3H), 7.40-7.51 (m, 2H), 7.27 (br t, J=7.53 Hz, 1H), 3.88 (s, 3H), 2.81-2.93 (m, 1H), 0.98-1.08 (m, 4H).

Comparative Example 2

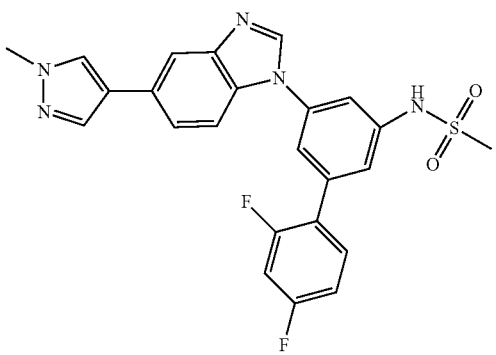

Compound B

The synthesis method was the same as that of Comparative Example 1, while cyclopropylsulfonamide was replaced by methanesulfonamide to obtain the trifluoroacetate salt of compound B. The trifluoroacetate salt of compound B was added to a sodium bicarbonate solution, and extracted with ethyl acetate. The organic phase was dried over anhydrous sodium sulfate and concentrated under reduced pressure to obtain compound B.

LCMS (ESI) m/z: 480.1 [M+1]$^+$;

$^1$H NMR (400 MHz, DMSO-d$_6$) δ 10.35 (s, 1H), 9.17 (s, 1H), 8.24 (s, 1H), 8.01 (s, 1H), 7.97 (s, 1H), 7.68-7.78 (m, 3H), 7.61 (br d, J=8.53 Hz, 2H), 7.49 (s, 1H), 7.38-7.47 (m, 1H), 7.27 (dt, J=2.13, 8.47 Hz, 1H), 3.88 (s, 3H), 3.18 (s, 3H).

Comparative Example 3

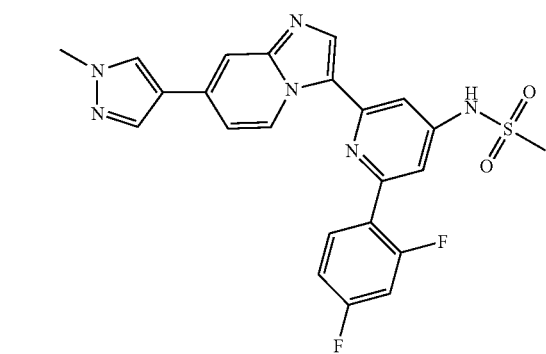

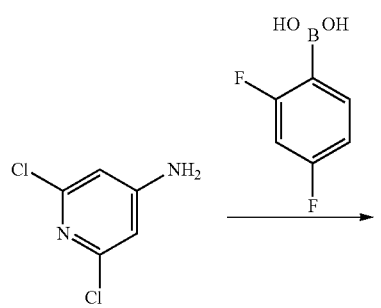

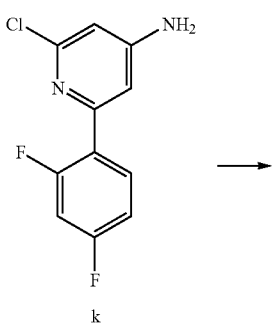

k

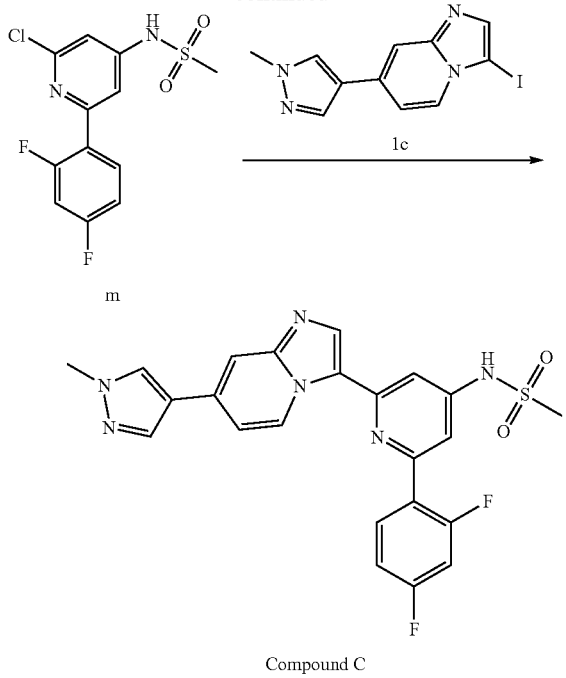

Compound C

Step One

Pd(dppf)Cl$_2$ (4.49 g, 6.13 mmol), K$_3$PO$_4$ (26.04 g, 122.70 mmol) was added to a solution of 2,6-dichloro-4-aminopyridine (10 g, 61.35 mmol) and (2,4-difluorobenzene)boronic acid (11.62 g, 73.62 mmol) in dioxane (100 mL)/water (30 (mL), and the reaction mixture was stirred at 100° C. for 16 hours under nitrogen protection. After the reaction mixture was completed, the liquid was separated, and the organic phase was concentrated under reduced pressure to obtain a crude product. The crude product was purified by column (flash silica gel column chromatography) with PE/Ethyl acetate=5/1 to obtain compound k.

LCMS (ESI) m/z: 240.9 [M+1]$^+$.

Step Two

Methanesulfonyl chloride (1.90 g, 16.62 mmol, 1.29 mL) was added to a solution of compound k (1 g, 4.16 mmol) in pyridine (10 mL) and stirred at 30° C. for 1 hour. Water (30 mL) was added to the reaction mixture, and then the mixture was extracted with ethyl acetate (30 mL*3), the organic phases were combined and dried over anhydrous sodium sulfate, and concentrated under reduced pressure to obtain a crude product. The crude product was purified by column (flash silica gel column chromatography) with PE/Ethyl acetate=3/1 to obtain compound m.

LCMS (ESI) m/z: 318.9 [M+1]$^+$.

Step 3

Compound 1c (0.1 g, 308.53 umol) was dissolved in DMF (3 mL), under nitrogen protection, hexabutyltin (268.47 mg, 462.79 umol, 231.44 uL), compound m (157.34 mg, 493.64 umol) were added, and then Pd(dppf)Cl$_2$·CH$_2$Cl$_2$ (125.98 mg, 154.26 umol) was added, and the reaction mixture was stirred at 110° C. for 16 hours under nitrogen protection, after the reaction was cooled to room temperature, the reaction mixture was added and quenched with potassium fluoride aqueous solution, and extracted with ethyl acetate, the organic phases were combined and concentrated under reduced pressure to obtain a crude product. The crude product was separated by preparative HPLC (chromatographic column: Welch Xtimate C18 150*25 mm*5 μm;

mobile phase: [water (0.225% trifluoroacetic acid)-acetonitrile]; B (acetonitrile) %: 15%-45%, 8.5 min) to obtain the formate of compound C. The the formate of compound C was added to a sodium bicarbonate solution, and extracted with ethyl acetate, the organic phase was dried over anhydrous sodium sulfate and concentrated under reduced pressure to obtain compound C.

LCMS (ESI) m/z: 481.1 [M+1]$^+$;

$^1$H NMR (400 MHz, METHANOL-d4) δ 9.97 (br d, J=7.28 Hz, 1H), 8.37 (br s, 1H), 8.26 (s, 1H), 8.01-8.13 (m, 2H), 7.69-7.84 (m, 1H), 7.65 (s, 1H), 7.50-7.57 (m, 2H), 7.05-7.22 (m, 2H), 3.98 (s, 3H), 3.23 (s, 3H).

Example 1

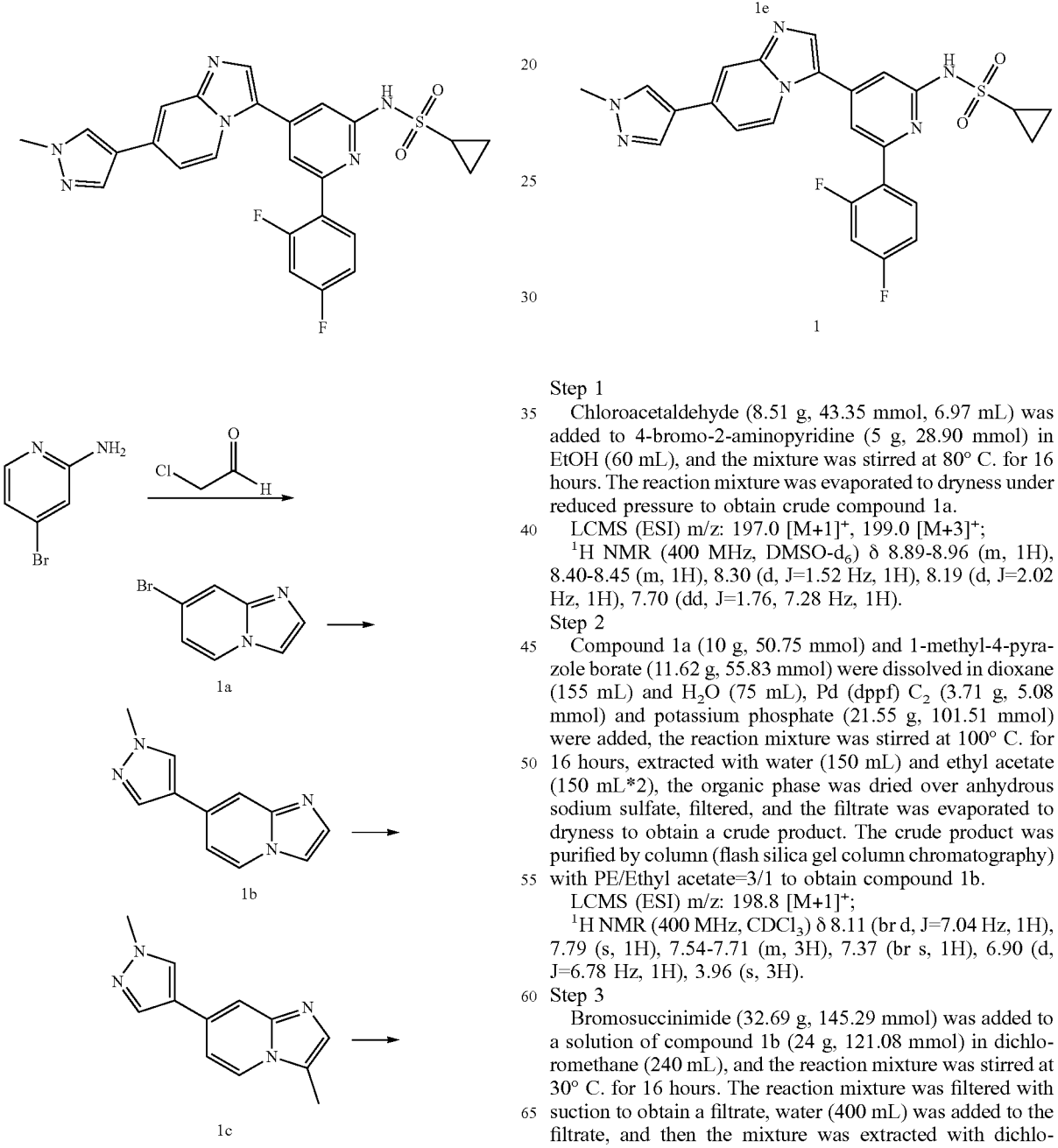

Step 1

Chloroacetaldehyde (8.51 g, 43.35 mmol, 6.97 mL) was added to 4-bromo-2-aminopyridine (5 g, 28.90 mmol) in EtOH (60 mL), and the mixture was stirred at 80° C. for 16 hours. The reaction mixture was evaporated to dryness under reduced pressure to obtain crude compound 1a.

LCMS (ESI) m/z: 197.0 [M+1]$^+$, 199.0 [M+3]$^+$;

$^1$H NMR (400 MHz, DMSO-d$_6$) δ 8.89-8.96 (m, 1H), 8.40-8.45 (m, 1H), 8.30 (d, J=1.52 Hz, 1H), 8.19 (d, J=2.02 Hz, 1H), 7.70 (dd, J=1.76, 7.28 Hz, 1H).

Step 2

Compound 1a (10 g, 50.75 mmol) and 1-methyl-4-pyrazole borate (11.62 g, 55.83 mmol) were dissolved in dioxane (155 mL) and H$_2$O (75 mL), Pd (dppf) C$_2$ (3.71 g, 5.08 mmol) and potassium phosphate (21.55 g, 101.51 mmol) were added, the reaction mixture was stirred at 100° C. for 16 hours, extracted with water (150 mL) and ethyl acetate (150 mL*2), the organic phase was dried over anhydrous sodium sulfate, filtered, and the filtrate was evaporated to dryness to obtain a crude product. The crude product was purified by column (flash silica gel column chromatography) with PE/Ethyl acetate=3/1 to obtain compound 1b.

LCMS (ESI) m/z: 198.8 [M+1]$^+$;

$^1$H NMR (400 MHz, CDCl$_3$) δ 8.11 (br d, J=7.04 Hz, 1H), 7.79 (s, 1H), 7.54-7.71 (m, 3H), 7.37 (br s, 1H), 6.90 (d, J=6.78 Hz, 1H), 3.96 (s, 3H).

Step 3

Bromosuccinimide (32.69 g, 145.29 mmol) was added to a solution of compound 1b (24 g, 121.08 mmol) in dichloromethane (240 mL), and the reaction mixture was stirred at 30° C. for 16 hours. The reaction mixture was filtered with suction to obtain a filtrate, water (400 mL) was added to the filtrate, and then the mixture was extracted with dichloromethane (200 mL*2), the organic phase was dried over anhydrous sodium sulfate and concentrated under reduced pressure to obtain a crude product. The crude product was purified by column (flash silica gel column chromatography) with dichloromethane/methanol=10/1 to obtain compound 1c.

LCMS (ESI) m/z: 325.0 [M+1]$^+$.

Step 4

Pd(dppf)Cl$_2$ (225.75 mg, 308.53 μmol) and potassium phosphate (1.31 g, 6.17 mmol) was added to a mixed solution of compound 1c (1 g, 3.09 mmol) and (2,6-dichloro-4-pyridine)boronic acid (650.96 mg, 3.39 mmol) in dioxane (10 mL) and water (3 mL). The reaction mixture was stirred at 120° C. for 1 hours under nitrogen protection in a microwave reactor. The reaction mixture was extracted with water (20 mL) and ethyl acetate (20 mL*2), the organic phase was dried over anhydrous sodium sulfate and concentrated under reduced pressure to obtain a crude product. The crude product was purified by column (flash silica gel column chromatography) with dichloromethane/methanol=10/1 to obtain compound 1d.

LCMS (ESI) m/z: 343.9 [M+1]$^+$.

Step 5

Potassium acetate (9.78 mg, 43.58 μmol), 4,5-bisdiphenylphosphino-9,9-dimethylxanthene (25.22 mg, 43.58 μmol, 0.2 eq) and cesium carbonate (425.97 mg, 1.31 mmol) were added to a solution of compound 1d (150 mg, 435.80 μmol) and methylsulfonamide (52.80 mg, 435.80 μmol) in dioxane (4 mL), the reaction mixture was stirred at 120° C. for 1 hour under nitrogen protection in a microwave reactor. The reaction mixture was filtered off with suction through celite, and the filtrate was concentrated under reduced pressure to obtain a crude product. The crude was purified by column (flash silica gel column chromatography) with dichloromethane/methanol=10/1 to obtain compound 1e.

LCMS (ESI) m/z: 429.0 [M+1]$^+$.

Step 6

Pd(dppf)Cl$_2$ (25.59 mg, 34.97 μmol) and potassium phosphate (222.71 mg, 1.05 mmol) were added to a solution of compound 1e (150 mg, 349.74 μmol), 2,4-difluorophenylboronic acid (90.00 mg, 569.94 μmol) in dioxane (3 mL)/water (1 mL), the reaction mixture was stirred at 100° C. for 16 hours under nitrogen protection. The reaction mixture was filtered, and the filtrate was concentrated under reduced pressure to obtain a crude product. The crude product was purified by high performance liquid chromatography (chromatographic column: Boston Green ODS 150 mm*30 mm*5 μm; mobile phase: [water (0.075% trifluoroacetic acid)-acetonitrile]; B (acetonitrile) %: 32%-52%, 12 min) to obtain the trifluoroacetate salt of compound 1. The trifluoroacetate salt of compound 1 was added to a sodium bicarbonate solution, and extracted with ethyl acetate. The organic phase was dried over anhydrous sodium sulfate and concentrated under reduced pressure to obtain compound 1.

LCMS (ESI) m/z: 507.0 [M+1]$^+$;

$^1$H NMR (400 MHz, MeOD) δ 8.78 (d, J=7.28 Hz, 1H), 8.39 (s, 1H), 8.30 (s, 1H), 8.17-8.26 (m, 1H), 8.16 (s, 1H), 8.05 (s, 1H), 7.83 (s, 1H), 7.78 (dd, J=1.52, 7.28 Hz, 1H), 7.39 (s, 1H), 7.10-7.20 (m, 2H), 4.00 (s, 3H), 3.08-3.20 (m, 1H), 1.20-1.32 (m, 2H), 1.04-1.14 (m, 2H).

The preparation of compound 2 in Table 1 was carried out with reference to the route of compound 1, except that 2,4-difluorophenylboronic acid used as the raw material in step 6 was replaced by the raw material B in the following table to obtain the trifluoroacetate of the corresponding compound. The trifluoroacetate salt of compound was added to a sodium bicarbonate solution, and extracted with ethyl acetate, the organic phase was dried over anhydrous sodium sulfate and concentrated under reduced pressure to obtain the corresponding compound.

TABLE 1

| Product No. | Product structure | Raw material B | Product LCMS m/z: [M + 1]$^+$ | Product $^1$H NMR |
|---|---|---|---|---|
| Compound 2 |  |  | 503.1 | Trifluoroacetate of compound 2 $^1$H NMR (400 MHz, CD$_3$OD): δ 8.83 (d, J = 7.3 Hz, 1H), 8.42 (s, 1H), 8.34 (s, 1H), 8.18 (s, 1H), 8.09 (d, J = 1.0 Hz, 1H), 7.81 (dd, J = 7.2, 1.6 Hz, 1H), 7.57 (dd, J = 8.4, 5.88 Hz, 1H), 7.51 (d, J = 1.3 Hz, 1H ), 7.42 (d, J = 1.32 Hz, 1H), 7.02-7.14 (m, 2H), 4.02 (s, 3H), 3.05-3.13 (m, 1H), 2.52 (s, 3H), 1.20-1.28 ( m, 2H), 1.03-1.10 ppm (m, 2H). |

Example 3

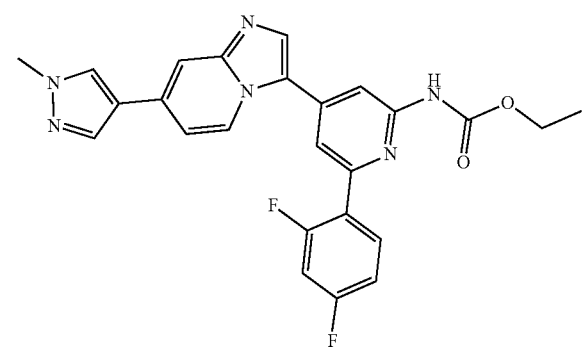 [SMILES: CCOC(=O)Nc1cc(-c2cnc3cc(-c4cnn(C)c4)ccn23)cc(-c2ccc(F)cc2F)n1]

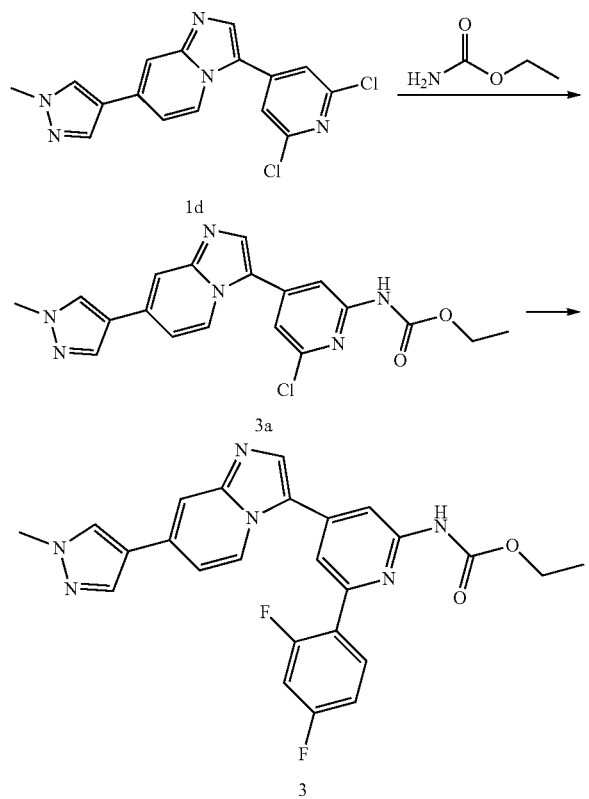

Step 1

Palladium acetate (32.61 mg, 145.27 μmol), 4,5-bis(diphenylphosphino)-9,9-dimethylxanthene (168.11 mg, 290.53 μmol) and cesium carbonate (1.42 g, 4.36 mmol) were added to a solution of compound 1d (0.5 g, 1.45 mmol), ethyl carbamate (110.01 mg, 1.23 mmol) in 1,4-dioxane (15 mL). The reaction mixture was stirred at 120° C. for 20 minutes under nitrogen protection in a microwave reactor. The reaction mixture was directly filtered, and the filtrate was concentrated under reduced pressure to obtain a crude product. The crude product was purified by silica gel column chromatography (DCM:MeOH=15:1) to obtain compound 3a.

LCMS (ESI) m/z: 397.1 [M+1]$^+$.

Step 2

Pd(dppf)Cl$_2$ (27.66 mg, 37.80 μmol), potassium phosphate (160.47 mg, 755.99 μmol) was added to a solution of compound 3a (150 mg, 378.00 μmol), 2,4-difluorophenylboronic acid (71.63 mg, 453.60 μmol) in THF (1.5 mL) and H$_2$O (0.5 mL). The reaction mixture was stirred at 100° C. for 30 minutes under nitrogen protection in microwave conditions. The reaction mixture was separated, the organic phase was concentrated under reduced pressure to obtain a crude product. The crude product was separated by preparative high performance liquid chromatography (chromatographic column: Boston Green ODS 150*30 mm*5 μm; mobile phase: [water (0.075% trifluoroacetic acid)-acetonitrile]; B (acetonitrile) %: 25%-55%, 8 min) to obtain the trifluoroacetate salt of compound 3. The trifluoroacetate salt of compound 3 was added to a sodium bicarbonate solution, and extracted with ethyl acetate. The organic phase was dried over anhydrous sodium sulfate and concentrated under reduced pressure to obtain compound 3.

LCMS (ESI) m/z: 475.1 [M+1]$^+$;

$^1$H NMR (400 MHz, CD$_3$OD) δ 8.81 (d, J=7.28 Hz, 1H), 8.37 (s, 1H), 8.24-8.31 (m, 2H), 8.12-8.21 (m, 2H), 8.03 (s, 1H), 7.71-7.81 (m, 2H), 7.05-7.19 (m, 2H), 4.27 (q, J=7.04 Hz, 2H), 4.00 (s, 3H), 1.35 (t, J=7.16 Hz, 3H).

The preparation of compound 4 in Table 2 was carried out with reference to the route of compound 3, except that 2,4-difluorophenylboronic acid used as the raw material in step 2 was replaced by raw material B in the following table to obtain the trifluoroacetate salt of the corresponding compound, the trifluoroacetate of the obtained compound was added to sodium bicarbonate solution, extracted with ethyl acetate, the organic phase was dried over anhydrous sodium sulfate, and concentrated under reduced pressure to obtain the corresponding compound.

TABLE 2

| Product No. | Product structure | Raw material B | Product LCMS m/z: [M + 1]$^+$ | Product $^1$H NMR |
|---|---|---|---|---|
| Compound 4 | | | 471.5 | Trifluoroacetate of compound 4 $^1$H NMR (400 MHz, CD$_3$OD) δ 8.87 (d, J = 7.04 Hz, 1H), 8.41 (s, 1H), 8.33 (s, 1H), 8.27 (s, 1H), 8.17 (s, 1H), 8.08 (s, 1H), 7.81 (br d, J = 7.04 Hz, 1H), 7.45-7.57 (m, 2H), 6.98-7.12 (m, 2H), 4.26 (q, J = 7.12 Hz, 2H), 4.00 (s, 3H), 2.46 (s, 3H), 1.35 (t, J = 7.16 Hz, 3H). |

Example 6

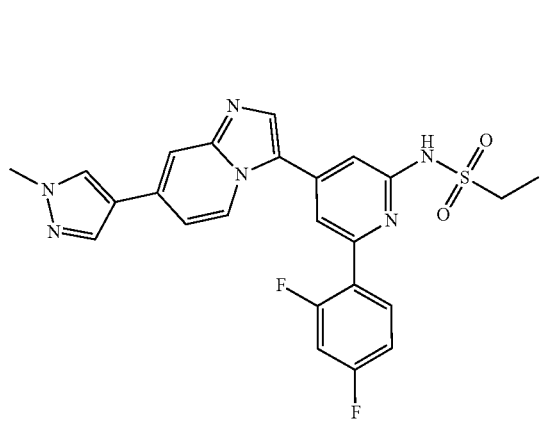 [SMILES: CCS(=O)(=O)Nc1cc(-c2cnc3cc(-c4cnn(C)c4)ccn23)cc(-c2ccc(F)cc2F)n1]

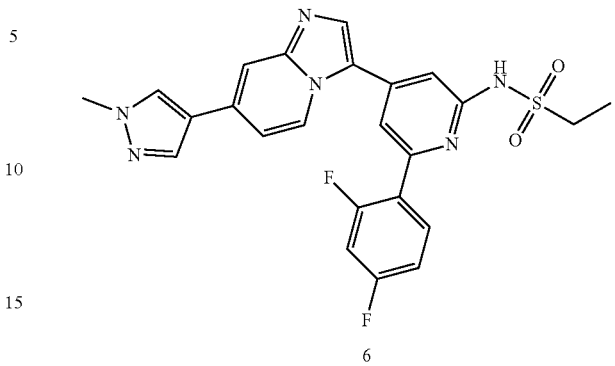

Step One

Compound 1d (200 mg, 581.06 μmol) and ethylsulfonamide (114.16 mg, 1.05 mmol) were dissolved in 1,4-dioxane (5 mL), palladium acetate (13.05 mg, 58.11 μmol), 4,5-bis(diphenylphosphino)-9,9-dimethylxanthene (67.24 mg, 116.21 μmol) and cesium carbonate (567.96 mg, 1.74 mmol) were added, the reaction mixture was stirred in microwave at 120° C. for 1 hour under nitrogen protection. The reaction mixture was directly filtered, the filter cake was washed with DCM/MeOH=10/1, and the filtrate was evaporated to dryness to obtain a crude product. The crude product was purified by a flash silica gel column (DCM/MeOH=10/1) to obtain compound 6a.

LCMS (ESI) m/z: 417.3 [M+1]$^+$.

Step Two

Compound 6a (0.2 g, 479.75 μmol) and 2,4-difluorophenylboronic acid (113.64 mg, 719.62 μmol) were dissolved in 1,4-dioxane (6 mL) and H$_2$O (3 mL), and potassium phosphate (305.51 mg, 1.44 mmol) and Pd(dppf)Cl$_2$ (35.10 mg, 47.97 μmol) were added, the reaction mixture was stirred at 100° C. for 16 hours under nitrogen protection. The reaction mixture was filtered and evaporated to dryness to obtain a crude product, and purified by preparative HPLC (chromatographic column: Boston Green ODS 150*30 mm*5 μm; mobile phase: [water (0.075% trifluoroacetic acid)-acetonitrile]; B (acetonitrile) %: 20%-50%, 7 min) to obtain a trifluoroacetate salt of compound 6. The trifluoroacetate salt of compound 6 was added to a sodium bicarbonate solution, and extracted with ethyl acetate. The organic phase was dried over anhydrous sodium sulfate and concentrated under reduced pressure to obtain compound 6.

LCMS (ESI) m/z: 495.0 [M+1]$^+$;

$^1$H NMR (400 MHz, CD$_3$OD) δ 8.80 (br d, J=7.34 Hz, 1H), 8.42 (s, 1H), 8.33 (s, 1H), 8.13-8.23 (m, 2H), 8.10 (s, 1H), 7.76-7.88 (m, 2H), 7.33 (s, 1H), 7.08-7.22 (m, 2H), 4.02 (s, 3H), 3.61 (q, J=7.36 Hz, 2H), 1.43 ppm (br t, J=7.36 Hz, 3H).

The preparation of the compounds in Table 3 was carried out with reference to the route of compound 6, except that ethyl sulfonamide used as the raw materials in step 1 was replaced by raw material B in the following table to obtain the dissociative corresponding compound or trifluoroacetates thereof, and the trifluoroacetates of the resulting compound were added respectively to sodium bicarbonate solution, extracted with ethyl acetate, the organic phase was dried over anhydrous sodium sulfate and concentrated under reduced pressure to obtain the corresponding compound.

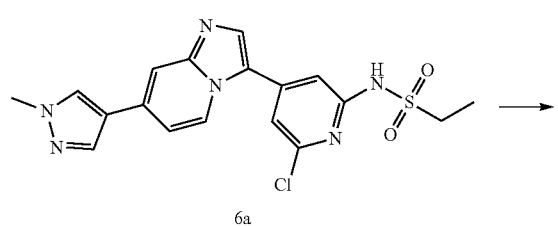

TABLE 3

| Product No. | Product structure | Raw material B | Product LCMS m/z: [M + 1]⁺ | Product ¹H NMR |
|---|---|---|---|---|
| Compound 7 | | H₂N-S(=O)₂-CH₃ | 481.0 | Trifluoroacetate of compound 7 ¹H NMR (400 MHz, CD₃OD) δ 8.78-8.84 (m, 1H), 8.39-8.43 (m, 1H), 8.31-8.34 (m, 1H), 8.16-8.25 (m, 2H) ), 8.06-8.10 (m, 1H), 7.84-7.88 (m, 1H), 7.78-7.83 (m, 1H), 7.30-7.34 (m, 1H), 7.12-7.22 (m, 2H), 4.02 (s, 3H), 3.43 ppm (s, 3H). |
| Compound 8 | | H₂N-S(=O)₂-propyl | 509.4 | Trifluoroacetate of compound 8 ¹H NMR (400 MHz, CD₃OD) δ 8.77-8.82 (m, 1H), 8.39-8.42 (m, 1H), 8.30-8.33 (m, 1H), 8.13-8.21 (m, 2H) ), 8.06-8.10 (m, 1H), 7.82-7.85 (m, 1H), 7.77-7.81 (m, 1H), 7.30-7.35 (m, 1H), 7.11-7.20 (m, 2H), 4.02 (s, 3H), 3.55-3.62 (m, 2H), 1.87-1.99 (m, 2H), 1.09 (t, J = 7.52 Hz, 3H). |
| Compound 9 | | H₂N-CH₂-C(CH₃)₂-OH | 475.1 | Compound 9 ¹H NMR (400 MHz, DMSO-d₆) δ 8.65-8.66 (d, J = 7.2 Hz, 1 H), 8.38 (s, 1 H), 8.10 (s, 1 H), 8.03-8.05 (m, 1 H), 7.90 (s, 1 H), 7.89 (s, 1 H), 7.29-7.36 (m, 2 H), 7.21-7.26 (m, 1 H), 7.14 (s, 1 H), 6.96 ( s, 1 H), 6.69-6.72 (m, 1 H), 4.69 (s, 1 H), 3.90 (s, 3 H), 3.38-3.39 (d, J = 5.6 Hz, 2 H), 1.18 (s, 6 H). |
| Compound 10 | | H₂N-(4-tetrahydropyranyl) | 487.3 | Compound 10 ¹H NMR (400 MHz, DMSO-d₆) δ 8.61-8.63 (d, J = 6.8 Hz, 1 H), 8.37 (s, 1 H), 8.10 (s, 1 H), 7.99-8.05 (m, 1 H), 7.88-7.90 (d, J = 8.4 Hz, 1 H), 7.32-7.37 (m, 1 H), 7.28-7.30 (d, J = 6.8 Hz, 1 H), 7.21-7.25 (t, J = 8.2 Hz, 1 H), 7.14 (s, 1 H), 6.82-6.84 (d, J = 6.8 Hz, 1 H), 6.79 (s, 1 H), 3.99-4.01 (s, 1 H), 3.89 |

TABLE 3-continued
| Product No. | Product structure | Raw material B | Product LCMS m/z: [M + 1]+ | Product 1H NMR |
|---|---|---|---|---|
| | | | | (s, 3 H), 3.43-3.48 (t, J = 10.8 Hz, 1 H), 3.31 (s, 4 H), 1.97-1.99 (d, J = 12.4 Hz, 2 H), 1.43-1.57 (m, 2 H). |
| Compound 11 | | H₂N with dioxolane | 517.3 | Compound 11 ¹H NMR (400 MHz, DMSO-d₆) δ 8.63-8.64 (d, J = 6.8 Hz, 1 H), 8.37 (s, 1 H), 8.04-8.10 (m, 2 H), 7.89-7.90 (d, J = 5.2 Hz, 2 H), 7.21-7.38 (m, 3 H), 7.17 (s, 1 H), 6.95-6.97 (t, J = 5.2 Hz, 1 H), 6.85 (s, 1 H), 4.30-4.35 (m, 1 H), 4.02-4.06 (m, 1 H), 3.89 (s, 3 H), 3.71-3.75 (m, 1 H), 3.52-3.54 (t, J = 5.2 Hz, 2 H), 1.38 (s, 3 H), 1.29 (s, 3 H). |
Example 12
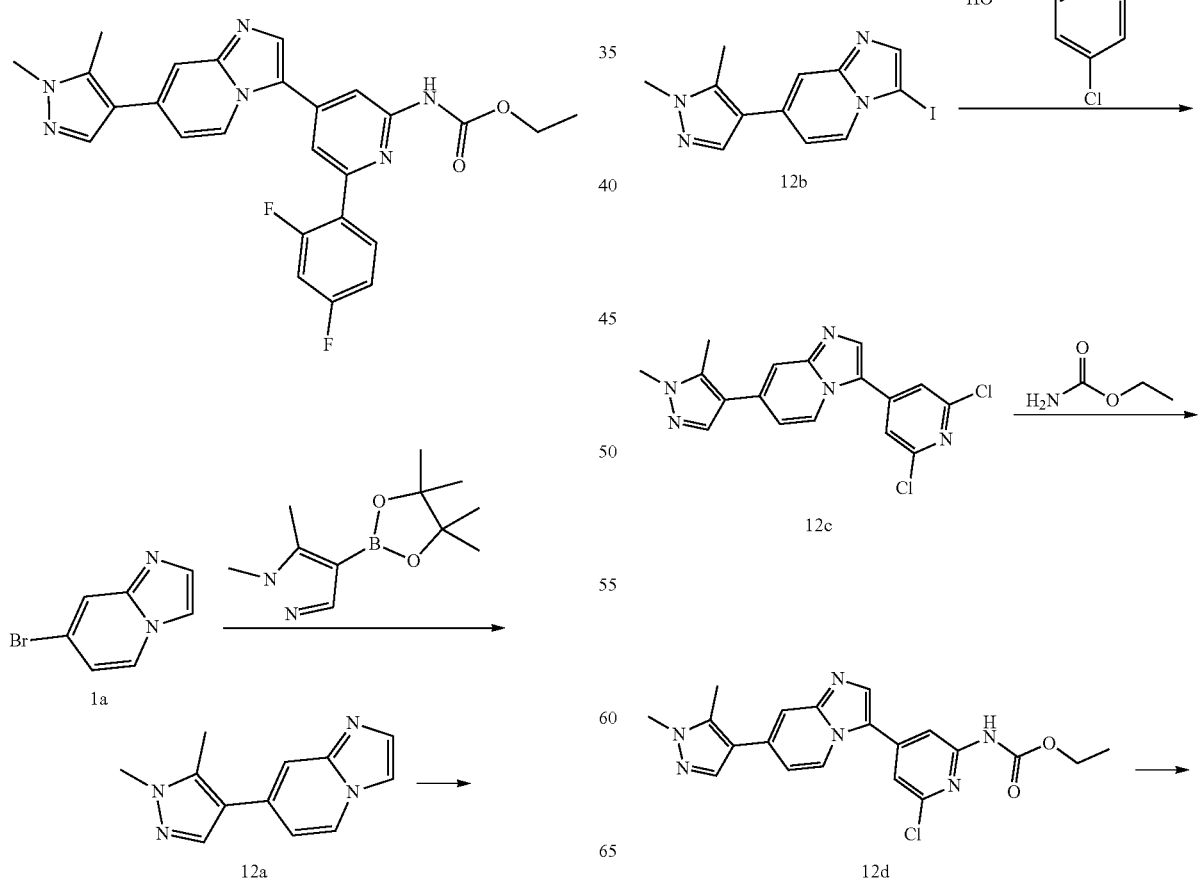

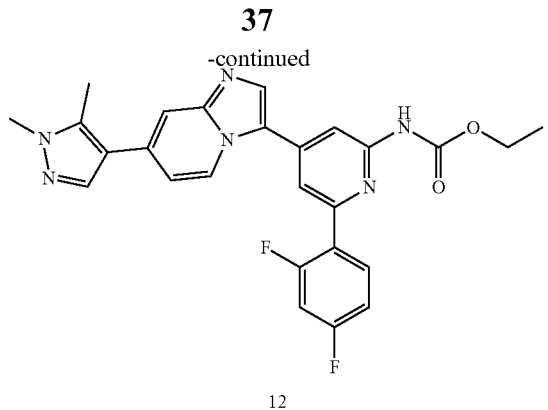

12

Step One

Pd(dppf)Cl$_2$ (1.86 g, 2.54 mmol), potassium phosphate (10.77 g, 50.75 mmol) was added to a solution of compound 1a (5 g, 25.38 mmol), 1,5-dimethyl-1H-pyrazole-4-boronic acid pinacol ester (6.20 g, 27.91 mmol) solution in dioxane (45 mL)/water (15 mL). The reaction mixture was stirred at 100° C. for 16 hours under nitrogen protection. The reaction mixture was filtered, water (100 mL) was added thereto, then the mixture was extracted with dichloromethane (100 mL*3), the organic phases were combined, dried over anhydrous sodium sulfate, and concentrated under reduced pressure to obtain a crude product. The crude product was purified by column (flash silica gel column chromatography) with dichloromethane/methanol=10/1 to obtain compound 12a.

LCMS (ESI) m/z: 212.9 [M+1]$^+$.

Step Two

NIS (152.64 mg, 678.45 μmol) was added to a solution of compound 12a (0.12 g, 565.37 μmol) in dichloromethane (5 mL), and the reaction mixture was stirred at 25° C. for 16 hours. The reaction mixture was extracted with water (10 mL) and dichloromethane (10 mL*3), the organic phases were combined, dried over anhydrous sodium sulfate, and concentrated under reduced pressure to obtain compound 12b.

LCMS (ESI) m/z: 338.9 [M+1]$^+$.

Step 3

Pd(dppf)Cl$_2$ (865.55 mg, 1.18 mmol), K$_3$PO$_4$ (5.02 g, 23.66 mmol) was added to a solution of compound 12b (2.72 g, 14.20 mmol) in dioxane (45 mL)/water (15 mL), the reaction mixture was stirred at 100° C. for 16 hours under nitrogen protection. The reaction mixture was filtered directly, water (100 mL) was added, and the mixture was extracted with ethyl acetate (100 mL*3), the organic phases were combined and dried over anhydrous sodium sulfate, and concentrated under reduced pressure to obtain a crude product. The crude product was purified by column (flash silica gel column chromatography) with dichloromethane/methanol=10/1 to obtain compound 12c.

LCMS (ESI) m/z: 358.1 [M+1]$^+$.

Step 4

Palladium acetate (9.40 mg, 41.87 μmol), cesium carbonate (409.29 mg, 1.26) mmol), Xantphos (48.46 mg, 83.75 μmol) were added to a solution of 12c (0.15 g, 418.73 μmol), ethyl carbamate (32 mg, 359.18 μmol) in dioxane (15 mL). The reaction mixture was stirred at 120° C. for 20 minutes under nitrogen protection in a microwave reactor. The reaction mixture was directly filtered, and the filtrate was concentrated under reduced pressure to obtain a crude product. The crude product was purified by preparative thin-layer chromatography silica gel plate (DCM:MeOH=15:1) to obtain compound 12d.

LCMS (ESI) m/z: 411.1 [M+1]$^+$.

Step 5

Pd(dppf)Cl$_2$ (5.34 mg, 7.30 μmol), K$_3$PO$_4$ (31.00 mg, 146.04 μmol) were added to a solution of 12d (30 mg, 73.02 μmol), 2,4-difluorophenylboronic acid (13.84 mg, 87.62 μmol) in tetrahydrofuran (1.5 mL)/water 0.5 mL). The reaction mixture was stirred at 100° C. for 30 minutes under nitrogen protection in microwave conditions. The reaction mixture was separated into layers, the organic phase was collected and concentrated under reduced pressure to obtain a crude product. The crude product was purified by preparative high performance liquid chromatography (chromatographic column: Welch Xtimate C18 100*25 mm*3 μm; mobile phase: [water (0.075% trifluoroacetic acid)-acetonitrile]; B (acetonitrile) %: 20%-50%, 8 min) to obtain a trifluoroacetate salt of compound 12. The trifluoroacetate salt of compound 12 was added to a sodium bicarbonate solution, and extracted with ethyl acetate. The organic phase was dried over anhydrous sodium sulfate and concentrated under reduced pressure to obtain compound 12.

LCMS (ESI) m/z: 489.2 [M+1]$^+$;

$^1$H NMR (400 MHz, MeOD-d$_4$) δ 8.85 (d, J=7.28 Hz, 1H), 8.28 (s, 2H), 8.11-8.22 (m, 1H), 7.85-7.97 (m, 2H), 7.79 (s, 1H), 7.65 (d, J=7.54 Hz, 1H), 7.04-7.19 (m, 2H), 4.27 (q, J=7.04 Hz, 2H), 3.91 (s, 3H), 2.60 (s, 3H), 1.35 (t, J=7.04 Hz, 3H).

Example 13

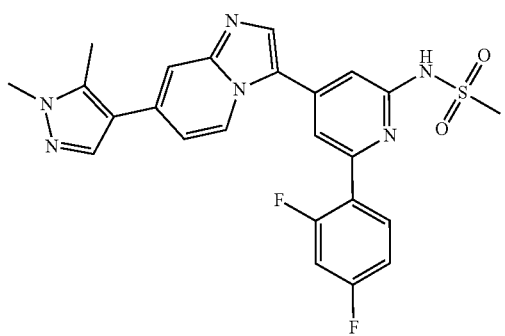

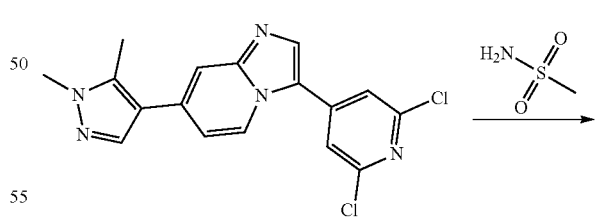

12c

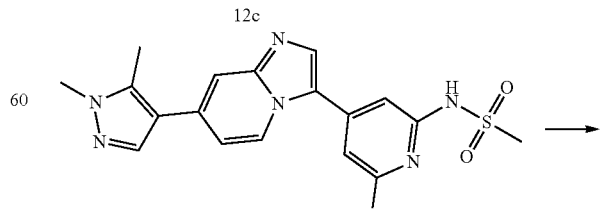

13a

-continued

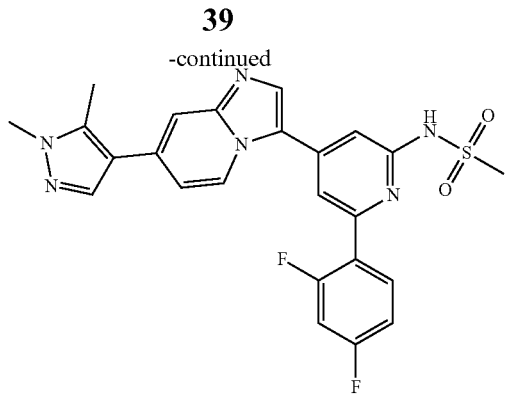

13

Step 1

Palladium acetate (15.67 mg, 69.79 µmol), Xantphos (80.76 mg, 139.58 µmol) and cesium carbonate (682.16 mg, 2.09 mmol) were added to a solution of 12c (0.25 g, 697.89 µmol), methanesulfonamide (132.77 mg, 1.40 mmol) in dioxane (5 mL). The reaction mixture was stirred at 120° C. for 1 hours under nitrogen protection in a microwave reactor. The reaction mixture was directly filtered with suction, and the filtrate was concentrated under reduced pressure to obtain a crude product. The crude product was separated by preparative TLC (DCM:MeOH=10:1) to obtain compound 13a.

LCMS (ESI) m/z: 417.0 [M+1]$^+$.

Step 2

Pd(dppf)Cl$_2$ (35.10 mg, 47.97 µmol), potassium phosphate (203.67 mg, 959.50 µmol) was added to a solution of 13a (200 mg, 479.75 µmol), 2,4-difluorophenylboronic acid (90.91 mg, 575.70 µmol) in tetrahydrofuran (1.5 mL)/water (0.5 mL), the reaction mixture was stirred at 100° C. for 45 minutes under the protection of nitrogen in a microwave reactor. Water (10 mL) was added to the reaction mixture, and then the mixture was extracted with ethyl acetate (10 mL*3), the organic phases were combined, dried over anhydrous sodium sulfate, and concentrated under reduced pressure to obtain a crude product. The crude product was separated by preparative thin-layer chromatography silica gel plate (DCM:MeOH=10:1) to obtain the crude product, which was separated by preparative high performance liquid chromatography (chromatographic column: Boston Green ODS 150*30 mm*5 µm; mobile phase: [water (0.075% trifluoroacetic acid)-acetonitrile]; B (acetonitrile) %: 23%-53%, 8 min) to obtain a trifluoroacetate salt of compound 13. The trifluoroacetate salt of compound 13 was added to a sodium bicarbonate solution, and extracted with ethyl acetate. The organic phase was dried over anhydrous sodium sulfate and concentrated under reduced pressure to obtain compound 13.

LCMS (ESI) m/z: 495.0 [M+1]$^+$;

$^1$H NMR (400 MHz, CD$_3$OD-d$_4$) δ 8.83 (d, J=7.28 Hz, 1H), 8.35 (s, 1H), 8.19 (dt, J=6.90, 8.85 Hz, 1H), 7.90-7.98 (m, 2H), 7.84 (s, 1H), 7.68-7.77 (m, 1H), 7.31 (d, J=1.00 Hz, 1H), 7.09-7.21 (m, 2H), 3.92 (s, 3H), 3.41 (s, 3H), 2.61 (s, 3H).

Biological Test Data:

Experimental Example 1: In Vitro Enzyme Activity Test of the Compounds of the Present Disclosure The IC$_{50}$ value was determined using $^{33}$P isotope-labeled kinase activity test (Reaction Biology Corp) to evaluate the inhibitory ability of the compounds to be tested on human FGFR1, FGFR2 and VEGFR2.

Buffer conditions: 20 mM Hepes (pH 7.5), 10 mM MgCl$_2$, 1 mM EGTA, 0.02% Brij35, 0.02 mg/mL BSA, 0.1 mM Na$_3$VO$_4$, 2 mM DTT, 1% DMSO.

Test steps: At room temperature, the compounds to be tested were dissolved in DMSO to prepare a 10 mM solution for use. The substrate was dissolved in the newly-prepared buffer, and the kinase to be tested was added thereto and mixed well. The DMSO solution in which the compounds to be tested were dissolved was added to the above-mentioned homogeneous reaction mixture using acoustic technology (Echo 550). The compound concentration in the reaction mixture was 10 µM, 2.50 µM, 0.62 µM, 0.156 µM, 39.1 nM, 9.8 nM, 2.4 nM, 0.61 nM, 0.15 nM, 0.038 nM or 3 µM, 1 µM, 0.333 µM, 0.111 µM, 37.0 nM, 12.3 nM, 4.12 nM, 1.37 nM, 0.457 nM, 0.152 nM. After incubating for 15 minutes, $^{33}$P-ATP (activity: 0.01 µCi/µL, with corresponding concentration listed in Table 4) was added to the reaction mixture to start the reaction. FGFR1, FGFR2, KDR and the concentration information in the reaction mixture were listed in Table 4. After the reaction was carried out at room temperature for 120 minutes, the reaction mixture was spotted on P81 ion exchange filter paper (Whatman #3698-915). After the filter paper was repeatedly washed with 0.75% phosphoric acid solution, the radioactivity of the phosphorylated substrate remaining on the filter paper was measured. The kinase activity data was expressed by comparing the kinase activity of the groups containing the compounds to be tested with that of the blank group (containing only DMSO). The IC$_{50}$ value was obtained by curve fitting using Prism4 software (GraphPad), and the experimental results were shown in Table 5.

TABLE 4

Related information about kinases, substrates and ATP in in-vitro tests.

| Kinase | Kinase concentration in reaction mixture (nM) | Substrate | Substrate concentration in reaction mixture (mg/L) | ATP concentration (µM) |
|---|---|---|---|---|
| FGFR1 Supplier: Invitrogen Cat #: PV3146 Lot #: 28427Q | 1.75 | pEY (mg/ml) + Mn Supplier: Sigma Cat #: P7244-250MG Lot #: 062K5104V | 0.2 mg/mL | 5 |
| VEGFR2 Supplier: Invitrogen Cat #: PR5992C Lot #: 36431DD | 1 | pEY (mg/ml) + Mn Supplier: Sigma Cat #: P7244-250MG Lot #: 062K5104V | 0.2 mg/mL | 10 |
| FGFR2 Supplier: Invitrogen Cat #: PV3368 | 0.45 | pEY (mg/ml) + Mn Supplier: Sigma Cat #: P7244-250MG Lot #: 062K5104V | 0.2 mg/mL | 5 |

TABLE 5

IC$_{50}$ test results of the kinase activity of the compounds of the present disclosure

| Compound number | FGFR1 IC$_{50}$(nM) | VEGFR2 IC$_{50}$(nM) | FGFR2 IC$_{50}$(nM) |
|---|---|---|---|
| Trifluoroacetate of compound A | 22.3 | 27.2 | 29.9 |
| Trifluoroacetate of compound B | N/A | 11.8 | 22.6 |

TABLE 5-continued

IC$_{50}$ test results of the kinase activity of the compounds of the present disclosure

| Compound number | FGFR1 IC$_{50}$(nM) | VEGFR2 IC$_{50}$(nM) | FGFR2 IC$_{50}$(nM) |
|---|---|---|---|
| Formate of compound C | 724 | 5580 | N/A |
| Trifluoroacetate salt of compound 1 | 4.55 | 3.82 | 2.86 |
| Trifluoroacetate salt of compound 2 | N/A | 67.3 | 46.1 |
| Trifluoroacetate salt of compound 3 | N/A | 1.99 | 3.26 |
| Trifluoroacetate salt of compound 4 | N/A | 24.3 | 45.2 |
| Trifluoroacetate salt of compound 6 | N/A | 8.09 | 7.36 |
| Trifluoroacetate salt of compound 7 | N/A | 2.94 | 3.22 |
| Trifluoroacetate salt of compound 8 | N/A | 14.7 | 7.18 |
| Compound 9 | N/A | 3.73 | 4.92 |
| Compound 10 | N/A | N/A | 17.1 |
| Compound 11 | N/A | 7.57 | 2.27 |
| Trifluoroacetate salt of compound 12 | N/A | 9.27 | 19.4 |
| Trifluoroacetate salt of compound 13 | N/A | 11.1 | N/A |

Note:
N/A means not tested.

Conclusion: The compound of the present disclosure has excellent FGFRs, VEGFR2 kinase activity. Compared with the trifluoroacetate of the control compounds A and B, the imidazopyridine mother nucleus compounds of the present disclosure increase nearly 4-10 times on FGFR1 or FGFR2 kinase and nearly 1-13 times on the activity of VEGFR2 kinase, it is very likely that it can demonstrate a better therapeutic effect at a lower dose clinically. Compared with the formate of the control compound C, the different introduced positions of the nitrogen atom on the aromatic ring in the middle of the compound of the present disclosure have a great influence on the activity, it was found that the activity of introducing heteroatom N at the 2 position of benzene ring sulfonamide in the present disclosure was significantly higher than that at the 4 position, and the activity of VEGFR2 was increased by 1000 times.

Experimental Example 2: Evaluation of the Pharmacokinetics of the Compound of the Present Disclosure Experimental procedure: 0.1 mg/mL 5% DMSO/10% solution 85% water clear solution of test compound was injected into female Balb/c mice (overnight fasting, 7-9 weeks old) through the tail vein, administration dose was 0.2 mg/kg. A clear solution of 0.1 mg/mL in 90% (25% HP-β-CD/10% polyoxyethylene castor oil (pH=4-5) of the test compound was intragastrically administered to female Balb/c mice (overnight fasting, 7-9 weeks old), the administration dose was 1 mg/kg. About 30 μL blood samples were collected from the jugular vein at 0.0833, 0.25, 0.5, 1.0, 2.0, 4.0, 8.0, 24 h after administration and from the tail vein at 0.25, 0.5, 1.0, 2.0, 4.0, 8.0, 24 h after administration, and the blood samples were put in an anticoagulation tube containing EDTA-K$_2$, the plasma was separated by centrifugation. The LC-MS/MS method was used to determine the blood drug concentration, the WinNonlin™ Version 6.3 (Pharsight, Mountain View, CA) pharmacokinetic software was used to calculate the relevant pharmacokinetic parameters by the non-compartmental model linear logarithmic ladder method.

Experimental Data Analysis:

TABLE 6

Summary table of pharmacokinetic data

| PK Parameters | Trifluoroacetate of reference compound A | | Trifluoroacetate of compound 1* | | Trifluoroacetate of compound 7 | |
|---|---|---|---|---|---|---|
| | IV 0.2 mg/kg | PO 1 mg/kg | IV 2 mg/kg | PO 10 mg/kg | IV 0.2 mg/kg | PO 1 mg/kg |
| C$_0$ (nM) | 563 | — | 7532 | — | 735 | — |
| C$_{max}$ (nM) | — | 469 | — | 5305 | — | 973 |
| T$_{max}$ (h) | — | 1.00 | — | 1.00 | — | 1.00 |
| T$_{1/2}$ (h) | 1.08 | 1.40 | 1.60 | 2.50 | 0.968 | 1.33 |
| Vd$_{ss}$ (L/kg) | 0.850 | — | 0.667 | — | 0.661 | — |
| Cl (mL/min/kg) | 9.20 | — | 4.82 | — | 7.96 | — |
| T$_{last}$ (h) | 4.00 | 8.00 | 8.00 | 8.00 | 4.00 | 8.00 |
| AUC$_{0-last}$ (nM·h) | 663 | 1408 | 13262 | 23556 | 810 | 2533 |
| AUC$_{0-inf}$ (nM·h) | 717 | 1444 | 13660 | 26911 | 871 | 2583 |
| MRT$_{0-last}$ (h) | 1.21 | 2.76 | 2.07 | 3.12 | 1.08 | 2.35 |
| F (%)$^a$ | — | 40.3 | — | 39.4 | — | 59.3 |

Note:
— means that the parameter cannot be calculated;
C$_0$ represents the initial concentration;
C$_{max}$ represents the peak concentration;
T$_{max}$ represents the peak time;
T$_{1/2}$ represents the elimination half-life;
Vd$_{ss}$ represents the steady-state apparent volume of distribution;
Cl represents the total clearance rate;
T$_{last}$ represents the last time point at which the drug can be quantified;
AUC$_{0-last}$ represents the area under the plasma concentration-time curve from time 0 to the last quantifiable time point;
AUC$_{0-inf}$ represents the area under the plasma concentration-time curve from time 0 to time point extrapolated to infinity;
MRT$_{0-las}$ represents the average residence time from time 0 to the last quantifiable time point;
F (%) represents the bioavailability.

Compared with the trifluoroacetate of the control compound A, the trifluoroacetate of compound 1 of the present disclosure has nearly decreased the plasma clearance rate by 1 time, doubled AUC of intravenous drug exposure, and nearly doubled the oral absorption drug exposure.

Experimental conclusion: The introduction of heterocyclic nitrogen atoms on the aromatic ring in the middle of the compound of the present disclosure significantly improves the metabolic stability of the compound and greatly improves the drug oral absorption drug exposure, and can demonstrate better pharmacokinetic oral absorption drug exposure and better therapeutic effect in the clinic.

Experimental Example 3: Anti-tumor Activity Test in an Animal Tumor Model In Vivo Experimental Objective:

To study the anti-tumor effect of the compounds of the present disclosure in a mouse subcutaneous xenograft tumor model of human gastric cancer SNU-16.

Experimental Method:

1) Preparation of Tumor Tissues

Preparation of tumor tissues: SNU-16 cells were routinely cultured in an RPMI-1640 culture medium containing 10% fetal bovine serum under the conditions of 5% CO$_2$, 37° C. and saturated humidity. According to cell growth, the cells were passaged or refilled 1 to 2 times a week with a passage ratio of 1:3 to 1:4.

2) Tissue Inoculation and Grouping

SNU-16 cells at the logarithmic growth phase were collected, counted and then resuspended in a 50% serum-free RPMI-1640 culture medium and 50% Matrigel, and cell concentration was adjusted to $4\times10^7$ cells/mL; the cells were placed in an ice box, and the cell suspension was suctioned with a 1 mL syringe, and subcutaneously injected into the anterior right axillary of nude mice, each animal was inoculated with 200 μL ($8\times10^6$ cells/mouse) to establish a SNU-16 xenograft model. The animal status was observed regularly, and the tumor diameter was measured with an electronic vernier caliper. The data was input into an Excel spreadsheet to calculate tumor volume and monitor tumor growth. Once the tumor volume reached 100 to 300 mm³, 60 tumor-bearing mice (tumor volume of 104 to 179 mm³) with good health and similar tumor volume were selected and divided into 10 (n=6) by a randomized block method, the average tumor volume of each group was about 143 mm³.

3) The tumor diameter was measured twice a week to calculate the tumor volume, and the animal body weight was weighed and recorded.

The calculation formula of tumor volume (TV) was: TV (mm³)=1×w²/2, where 1 represented the long diameter of the tumor (mm); w represented the short diameter of the tumor (mm).

The anti-tumor efficacy of the compounds was evaluated by TGI (%) or relative tumor proliferation rate T/C (%). Relative tumor proliferation rate T/C (%)=$T_{RTV}/C_{RTV}\times$100% ($T_{RTV}$: the mean RTV of the treatment group; $C_{RTV}$: the mean RTV of the negative control group). The relative tumor volume (RTV) was calculated according to the results of the tumor measurement. The calculation formula was RTV=$V_t/V_0$, where $V_0$ was the tumor volume measured at the beginning of the grouping and administration (i.e., D0), and $V_t$ was the tumor volume corresponding to a certain measurement in the mouse. $T_{RTV}$ and $C_{RTV}$ were obtained from the data on the same day.

TGI (%) reflected the tumor growth inhibition rate. TGI (%): TGI (%)=[(1 (average tumor volume at the end of administration in a certain treatment group–average tumor volume at the beginning of administration in the treatment group))/(average tumor volume at the end of administration in the solvent control group–average tumor volume at the beginning of administration in the solvent control group)]×100%.

Figure 2:
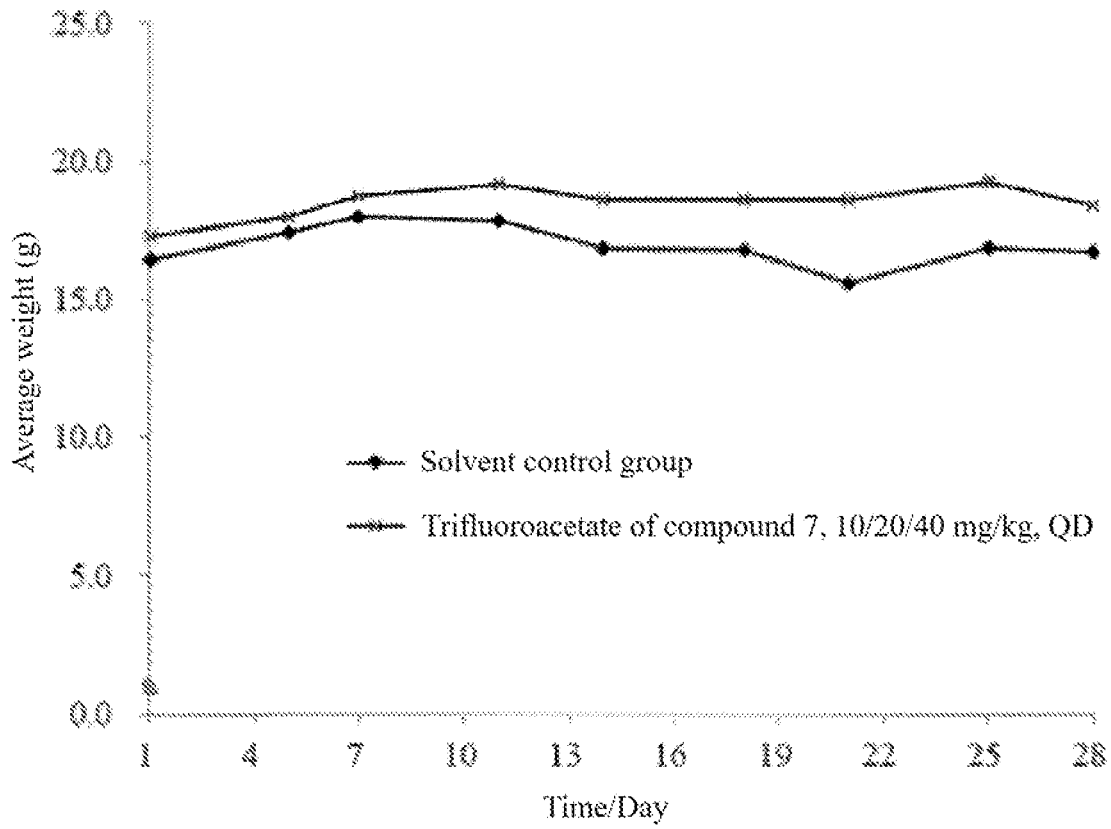
FIG. 2: The animal body weight change curve of each group during the administration period.

Experimental Results:

In the mouse model of gastric cancer SNU-16, the compounds of the present disclosure showed significant anti-tumor activity compared with the solvent group after continuous administration for 28 days, the tumor growth inhibition rates (% TGI) were: 69% respectively; and the relative tumor proliferation rates (% T/C) were: 31%. The specific results were shown in Table 7, FIG. 1 and FIG. 2 (QD represents once a day in the Figs).

TABLE 7

Summary table of SNU-16 tumor growth inhibition rate and relative tumor proliferation rate

| | Dosage (PO)* | TGI (%) (tumor growth inhibition rate) D25 | T/C (%) (relative tumor proliferation rate) D25 | P value |
|---|---|---|---|---|
| Trifluoroacetate of compound 7 | 10/20/40 mg/kg | 69% | 31% | <0.01 |

*In all administration groups, the dosage on day 8 was changed to 20 mg/kg/day, and the dosage on day 17 was changed to 40 mg/kg/day.

Experimental Conclusion: The Compound of the Present Disclosure Shows Significant Anti-Tumor Activity.

What is claimed is:

1. A compound represented by formula (I) or a pharmaceutically acceptable salt thereof,

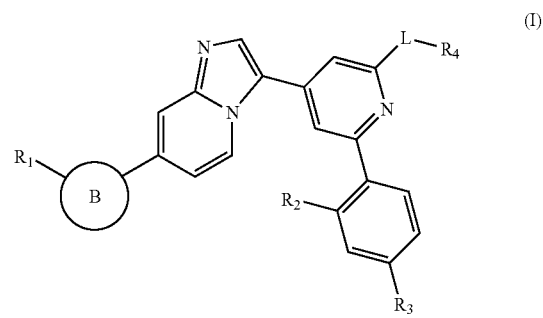

wherein,
$R_1$ is selected from H and $C_{1-3}$ alkyl optionally substituted by 1, 2 or 3 $R_a$;
$R_2$ and $R_3$ are each independently selected from H, F, Cl, Br, I, OH, $NH_2$ and $CH_3$;
$R_4$ is selected from H, $C_{1-6}$ alkyl, $C_{1-3}$ alkoxy, $C_{3-5}$ cycloalkyl, tetrahydropyranyl and 1,3-dioxolanyl, wherein, the $C_{1-6}$ alkyl, $C_{1-3}$ alkoxy, $C_{3-5}$ cycloalkyl, tetrahydropyranyl and 1,3-dioxolanyl are optionally substituted by 1, 2 or 3 $R_b$;
L is selected from —N($R_5$)C(=O)—, —N($R_5$)S(=O)$_2$—, —N($R_5$)C(=O)N($R_5$)—, —N($R_5$)CH$_2$— and —N($R_5$)—;
$R_5$ is each independently selected from H and $C_{1-3}$ alkyl;
ring B is selected from pyrazolyl and imidazolyl, the pyrazolyl and imidazolyl are optionally substituted by 1 or 2 $R_6$;
$R_6$ is selected from H and $C_{1-3}$ alkyl;
$R_a$ and $R_b$ are each independently selected from H, F, Cl, Br, I, OH, $NH_2$, CN and $CH_3$.

2. The compound according to claim 1 or the pharmaceutically acceptable salt thereof, wherein $R_1$ is selected from H, $CH_3$ and $CH_2CH_3$, and the $CH_3$ and $CH_2CH_3$ are optionally substituted by 1, 2 or 3 $R_a$.

3. The compound according to claim 2 or the pharmaceutically acceptable salt thereof, wherein $R_1$ is selected from H, $CH_3$, $CH_2OH$, $CH_2CH_2OH$ and $CH_2CH_3$.

4. The compound according to claim 1 or the pharmaceutically acceptable salt thereof, wherein $R_4$ is selected from H, cyclopropyl, $CH_3$, $CH_2CH_3$, $CH(CH_3)_2$, $C(CH_3)_3$, $CH_2CH_2CH_3$, $CH_2CH(CH_3)_2$, $OCH_3$, $OCH_2CH_3$, tetrahydropyranyl and 1,3-dioxolanyl, the cyclopropanyl, $CH_3$, $CH_2CH_3$, $CH(CH_3)_2$, $C(CH_3)_3$, $CH_2CH_2CH_3$, $CH_2CH(CH_3)_2$, $OCH_3$, $OCH_2CH_3$, tetrahydropyranyl and 1,3-dioxolanyl are optionally substituted by 1, 2 or 3 $R_b$.

5. The compound according to claim 4 or the pharmaceutically acceptable salt thereof, wherein $R_4$ is selected from H,

$CH_3$, $CH_2CH_3$, $CH(CH_3)_2$, $C(CH_3)_3$, $CH_2CH_2CH_3$, $OCH_2CH_3$,

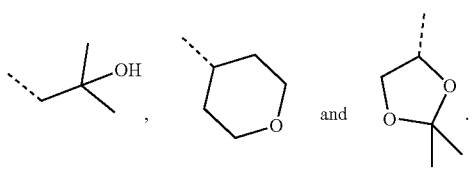

6. The compound according to claim 1 or the pharmaceutically acceptable salt thereof, wherein $R_5$ is independently selected from H, $CH_3$ and $CH_2CH_3$.

7. The compound according to claim 6 or the pharmaceutically acceptable salt thereof, wherein L is selected from —NHC(=O)—, —NHC(=O)NH—, —NHS(=O)$_2$—, —NHCH$_2$— and —NH—.

8. The compound according to claim 5 or the pharmaceutically acceptable salt thereof, wherein -L-R$_4$ is selected from

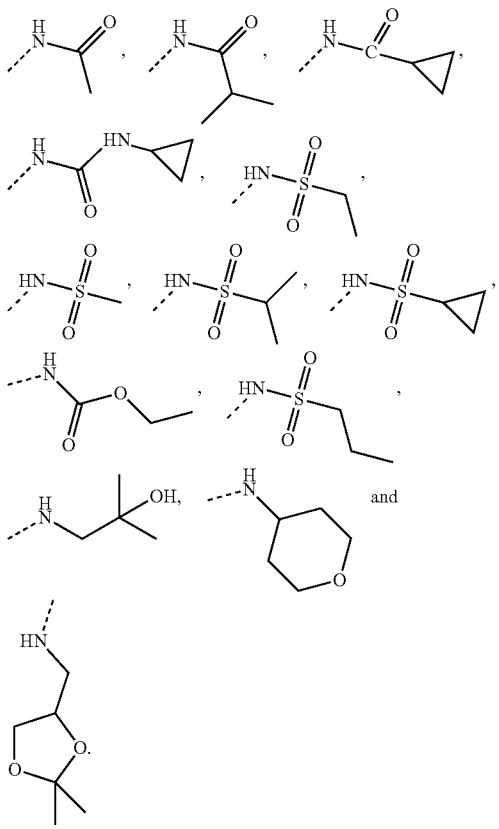

9. The compound according to claim 1 or the pharmaceutically acceptable salt thereof, wherein ring B is selected from

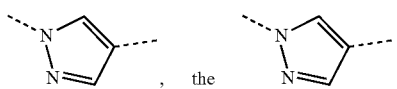

is optionally substituted by 1 or 2 R$_6$.

10. The compound according to claim 9 or the pharmaceutically acceptable salt thereof, wherein ring B is selected from

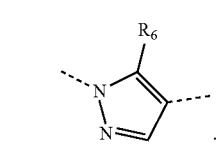

11. The compound according to claim 10 or the pharmaceutically acceptable salt thereof, wherein the structural moiety

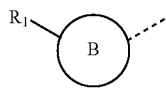

is selected from

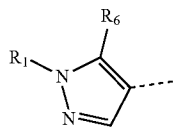

12. The compound according to claim 11 or the pharmaceutically acceptable salt thereof, wherein the structural moiety

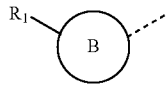

is selected from

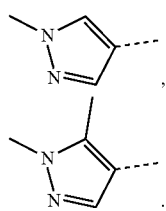
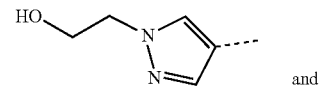

13. The compound according to claim 1 or the pharmaceutically acceptable salt thereof, wherein the compound is selected from

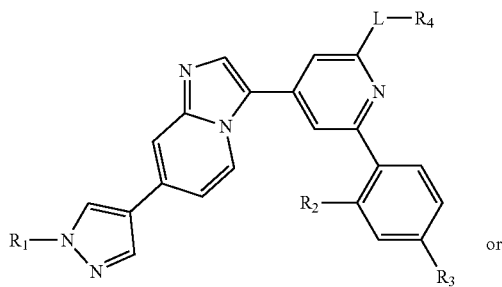

or

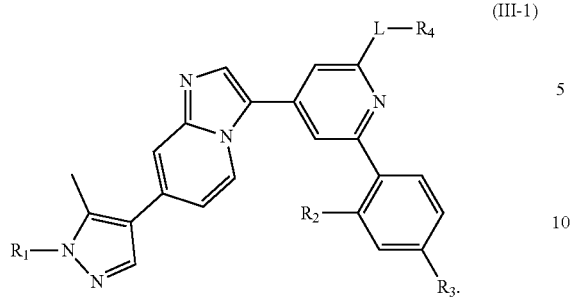
(III-1)
14. The compound according to claim 13 or the pharmaceutically acceptable salt thereof, wherein the compound is selected from the group consisting of:
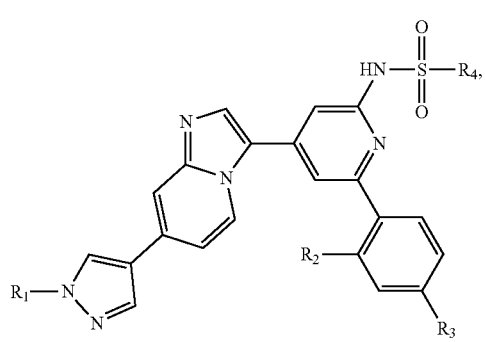
(I-1a)
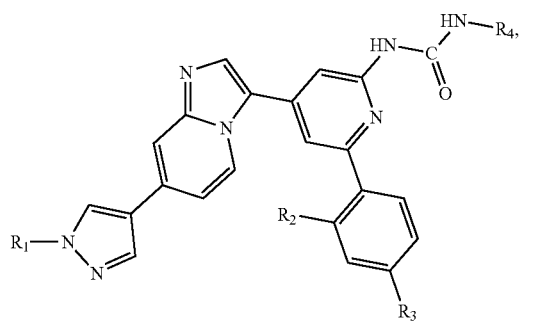
(I-1b)
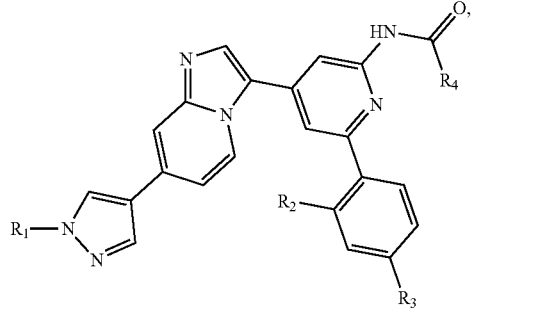
(I-1c)
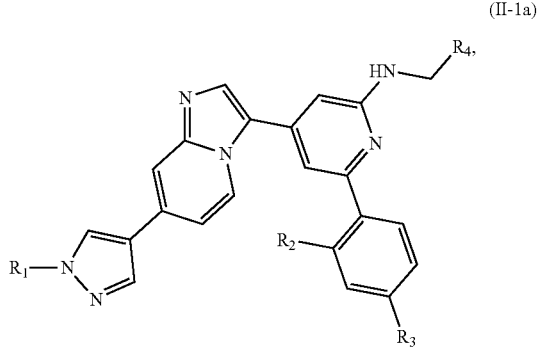
(II-1a)
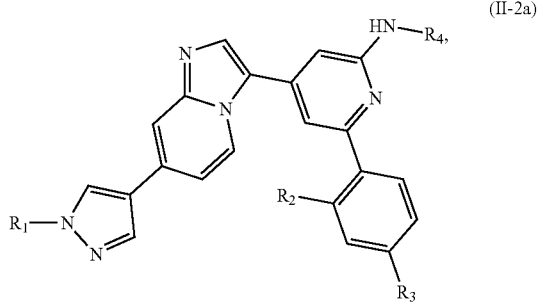
(II-2a)
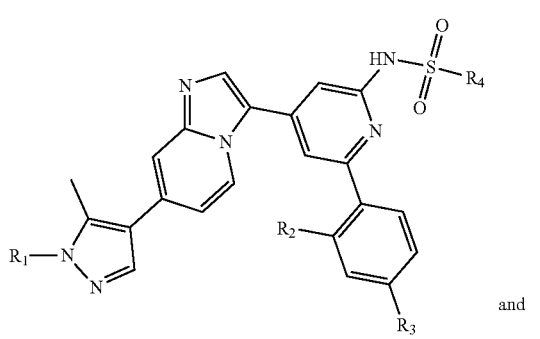
(III-1a)
and
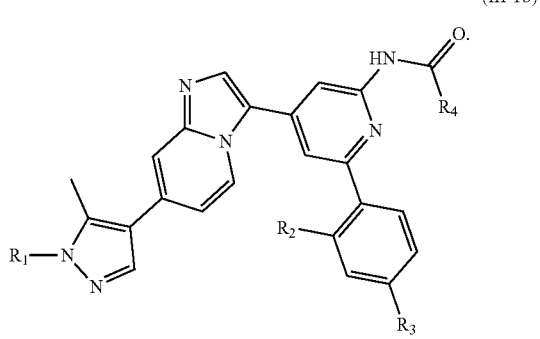
(III-1b)
15. A compound or a pharmaceutically acceptable salt thereof, wherein the compound is selected from the group consisting of:

49
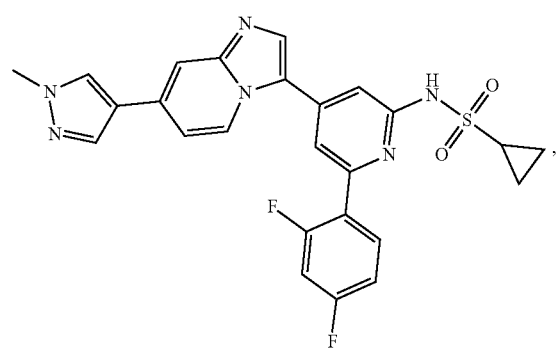
50
-continued
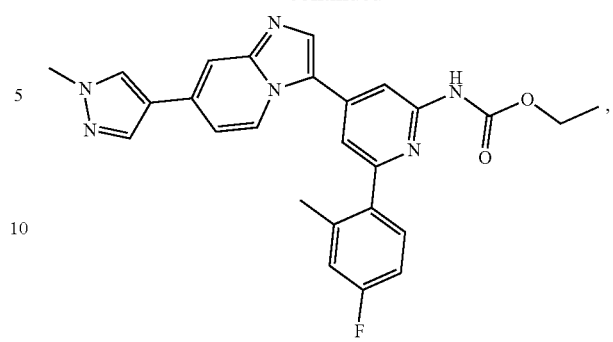
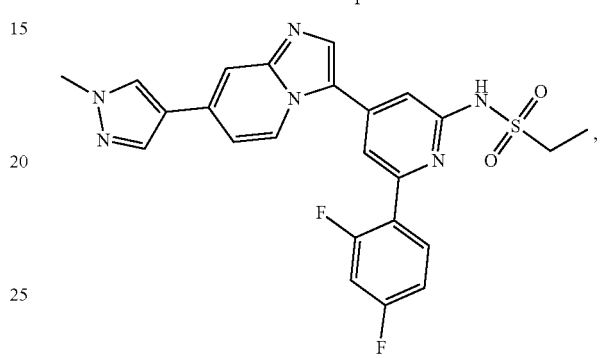
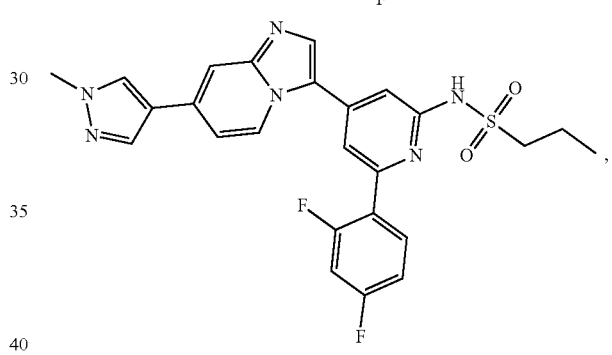
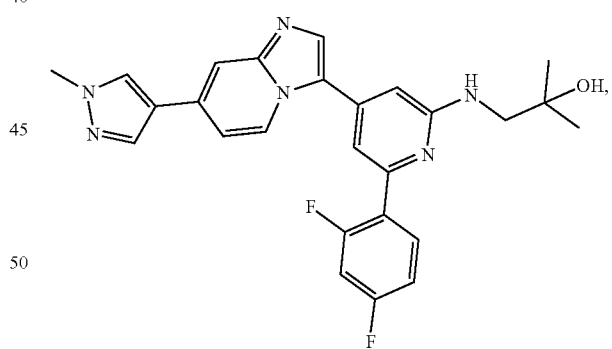
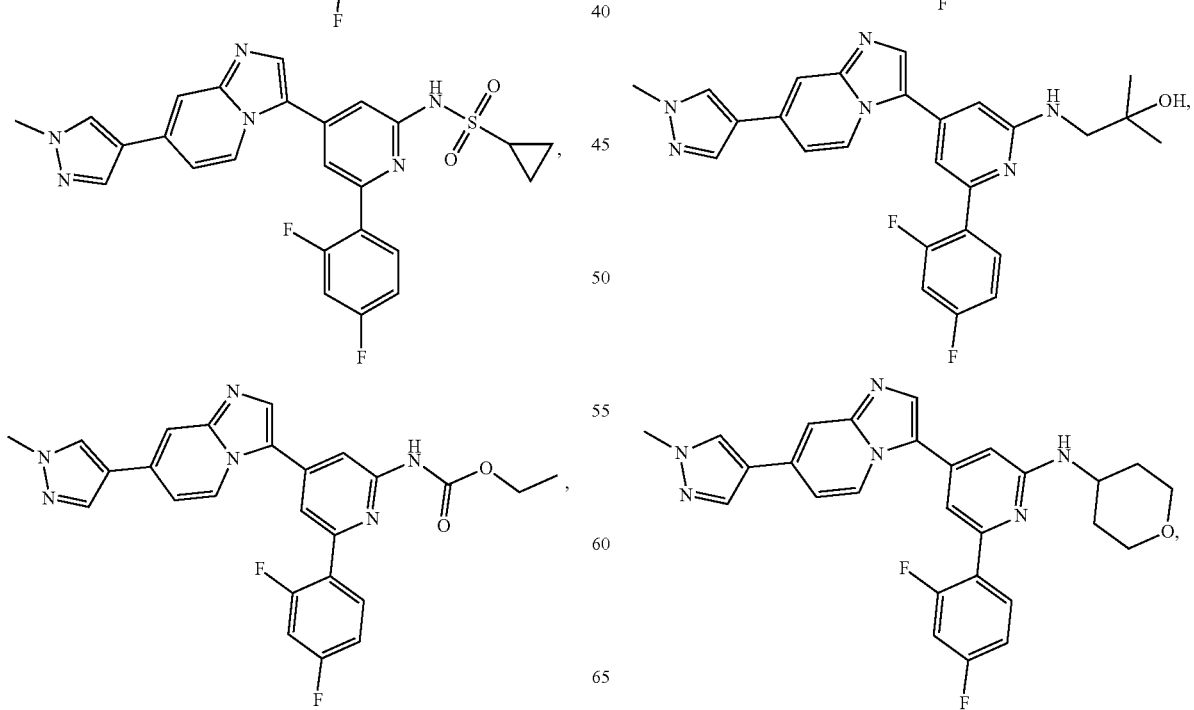

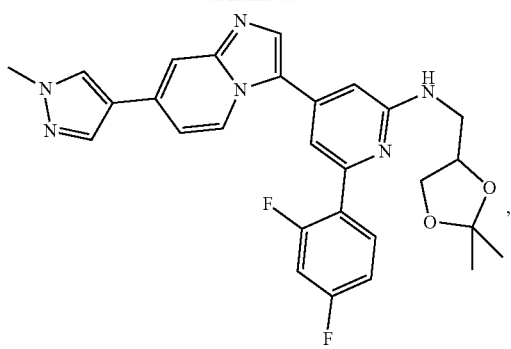

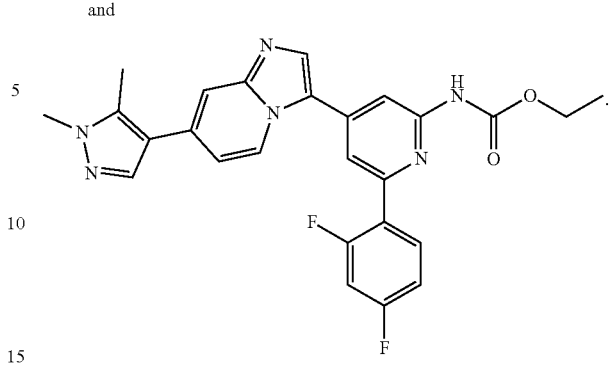

16. A pharmaceutical composition, comprising a therapeutically effective amount of the compound according to claim 1 or the pharmaceutically acceptable salt thereof as an active ingredient and a pharmaceutically acceptable carrier.

17. A method for inhibiting FGFR and VEGFR in a subject in need thereof, comprising administering an effective amount of the compound according to claim 1 or the pharmaceutically acceptable salt thereof to the subject.

18. A method for treating solid tumors in a subject in need thereof, comprising administering an effective amount of the compound according to claim 1 or the pharmaceutically acceptable salt thereof to the subject.

19. A method for inhibiting FGFR and VEGFR in a subject in need thereof, comprising administering an effective amount of the composition according to claim 16 to the subject.

20. A method for treating solid tumors in a subject in need thereof, comprising administering an effective amount of the composition according to claim 16 to the subject.

* * * * *